(12) United States Patent
Goldman

(10) Patent No.: US 9,682,043 B2
(45) Date of Patent: Jun. 20, 2017

(54) METHOD OF PREPARATION OF MIXED PHASE CO-CRYSTALS WITH ACTIVE AGENTS

(75) Inventor: David Goldman, Portland, CT (US)

(73) Assignee: MedCrystalForms, LLC, Hunt Valley, MD (US)

( * ) Notice: Subject to any disclaimer, the term of this patent is extended or adjusted under 35 U.S.C. 154(b) by 537 days.

(21) Appl. No.: 11/008,034

(22) Filed: Dec. 9, 2004

(65) Prior Publication Data

US 2005/0181041 A1  Aug. 18, 2005

Related U.S. Application Data

(60) Provisional application No. 60/528,232, filed on Dec. 9, 2003, provisional application No. 60/559,862, filed on Apr. 6, 2004.

(51) Int. Cl.
| | | |
|---|---|---|
| *A61K 9/14* | (2006.01) | |
| *A61K 8/63* | (2006.01) | |
| *A61K 9/48* | (2006.01) | |
| *A61K 9/10* | (2006.01) | |

(52) U.S. Cl.
CPC ............... *A61K 9/145* (2013.01); *A61K 8/63* (2013.01); *A61K 9/146* (2013.01); *A61K 9/148* (2013.01); *A61K 9/10* (2013.01); *A61K 9/4858* (2013.01)

(58) Field of Classification Search
None
See application file for complete search history.

(56) References Cited

U.S. PATENT DOCUMENTS

| | | | |
|---|---|---|---|
| 4,384,980 A | 5/1983 | Patel et al. | |
| 4,606,909 A * | 8/1986 | Bechgaard et al. | 424/469 |
| 5,118,528 A | 6/1992 | Fessi et al. | |
| 5,266,712 A * | 11/1993 | Lanquetin | 552/574 |
| 5,665,331 A | 9/1997 | Bagchi et al. | |
| 2002/0142049 A1* | 10/2002 | Lee | 424/499 |
| 2003/0003155 A1* | 1/2003 | Kipp et al. | 424/489 |
| 2003/0031721 A1 | 2/2003 | Bogue | |
| 2003/0049323 A1* | 3/2003 | Hitt et al. | 424/489 |
| 2003/0068384 A1 | 4/2003 | Brocchini et al. | |
| 2003/0077297 A1* | 4/2003 | Chen et al. | 424/400 |
| 2003/0077329 A1* | 4/2003 | Kipp et al. | 424/489 |
| 2003/0166509 A1 | 9/2003 | Edwards et al. | |

FOREIGN PATENT DOCUMENTS

| | | | |
|---|---|---|---|
| JP | 63-240936 A | 10/1988 | |
| JP | 2003-522097 A | 8/1999 | |
| JP | 2002506876 A | 3/2002 | |
| JP | 2002356419 A | 12/2002 | |
| WO | WO 99/47543 A2 | 9/1999 | |
| WO | WO 02/055059 A2 | 7/2002 | |
| WO | WO 03/101392 A2 | 12/2003 | |
| WO | WO 2004/043358 | 5/2004 | |
| WO | WO 2004/078161 A1 | 9/2004 | |
| WO | WO 2004/082666 | 9/2004 | |

OTHER PUBLICATIONS

Lide CRC Handbook of Chemistry and Physics 2003 p. 3-246 and 3-480.*
Meyerson et al. "Crystals, Crystal Growth, and Nucleation" Handbook of Industrial Crystallization Ed. Meyerson. Woburn: Butterworth-Heinemann 2002 p. 33, and 38-39.*
Payne et al. International Journal of Pharmaceutics 1999 177:231-245.*
Zhang et al. Journal of Pharmaceutical Sciences 2007 96(5):990-995.*
Reutzel-Edens et al. Solid-state pharmaceutical development: Ensuring stability through salt and polymorph screening. Pharmaceutical Stress Testing. Ed. Baertschi et al. New York:Informa Healthcare 2011 p. 254 and 266-267.*
Drenth Principles of Protein X-ray Crystallography 1999 New York:Springer Science+Business Media p. 19.*
International Search Report for PCT/US2004/041500 (Oct. 6, 2006).
Khan et al, "Stability characterization of controlled release coprecipitates and solid dispersions," Journal of Controlled Release, Elsevier Science Publishers B.V., vol. 63, No. 1-2, Jan. 2000.
Japanese Patent Office, Office Action in connection with Japanese Patent Application No. 149502/2011 (May 7, 2013).
Japanese Patent Office, Office Action in connection with Japanese Patent Application No. 182177/2014 (May 24, 2016).
Japanese Patent Office, Office Action in connection with Japanese Patent Application No. 182177/2014 (Aug. 18, 2015).

* cited by examiner

*Primary Examiner* — Robert A Wax
*Assistant Examiner* — Caralynne Helm
(74) *Attorney, Agent, or Firm* — Leydig, Voit & Mayer, Ltd.

(57) ABSTRACT

This invention pertains to a method of preparing mixed phase co-crystals of active agents with one or more materials that allows the modification of the active agent to a new physical/crystal form with unique properties useful for the delivery of the active agent, as well as compositions comprising the mixed phase co-crystals.

1 Claim, 8 Drawing Sheets

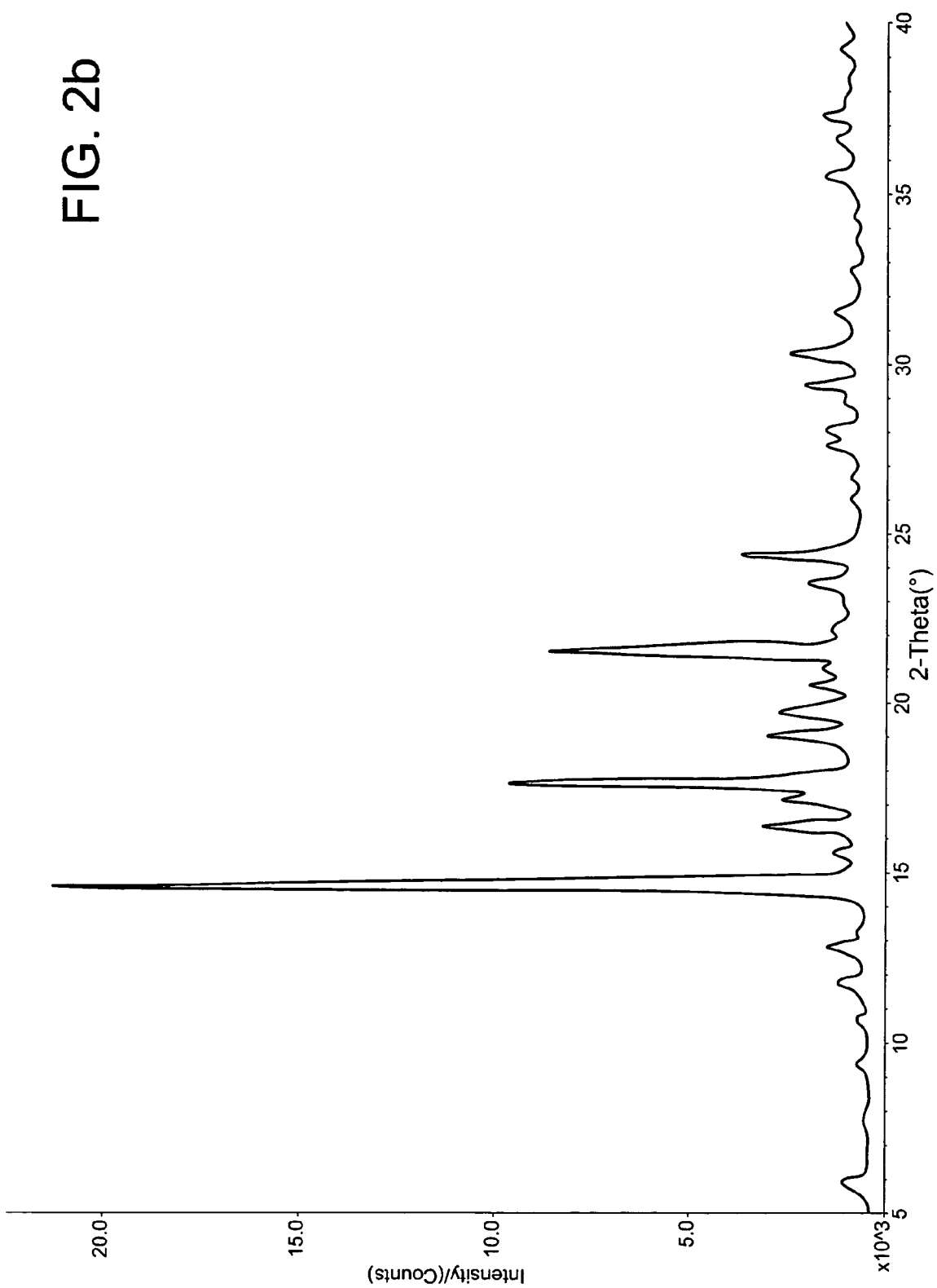

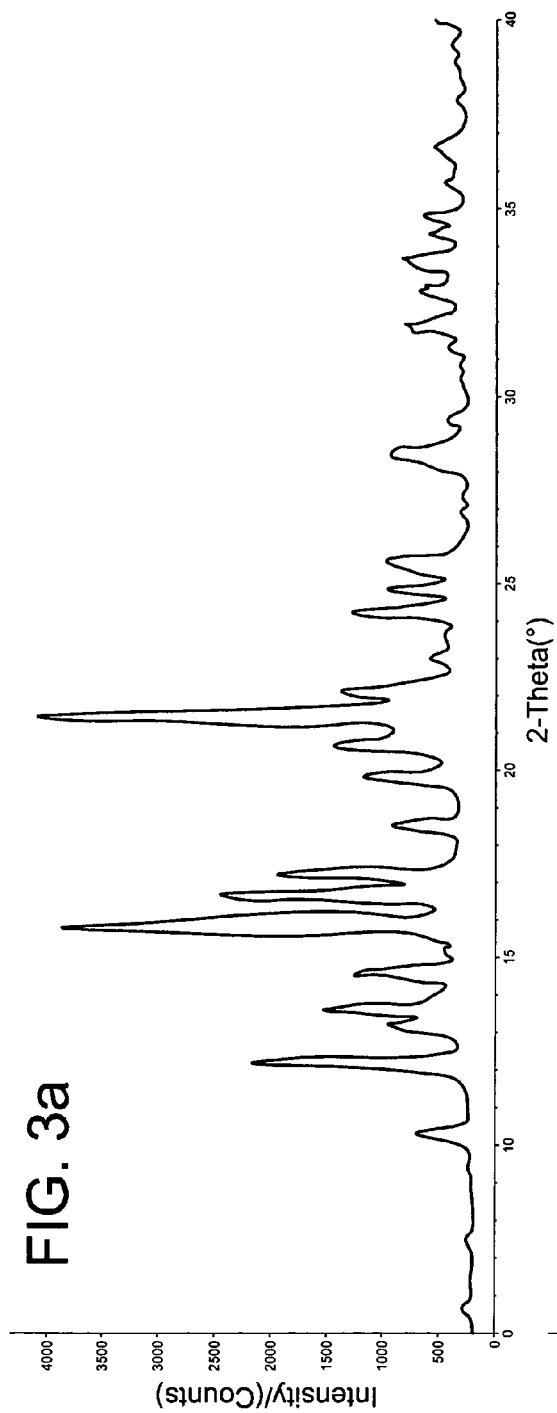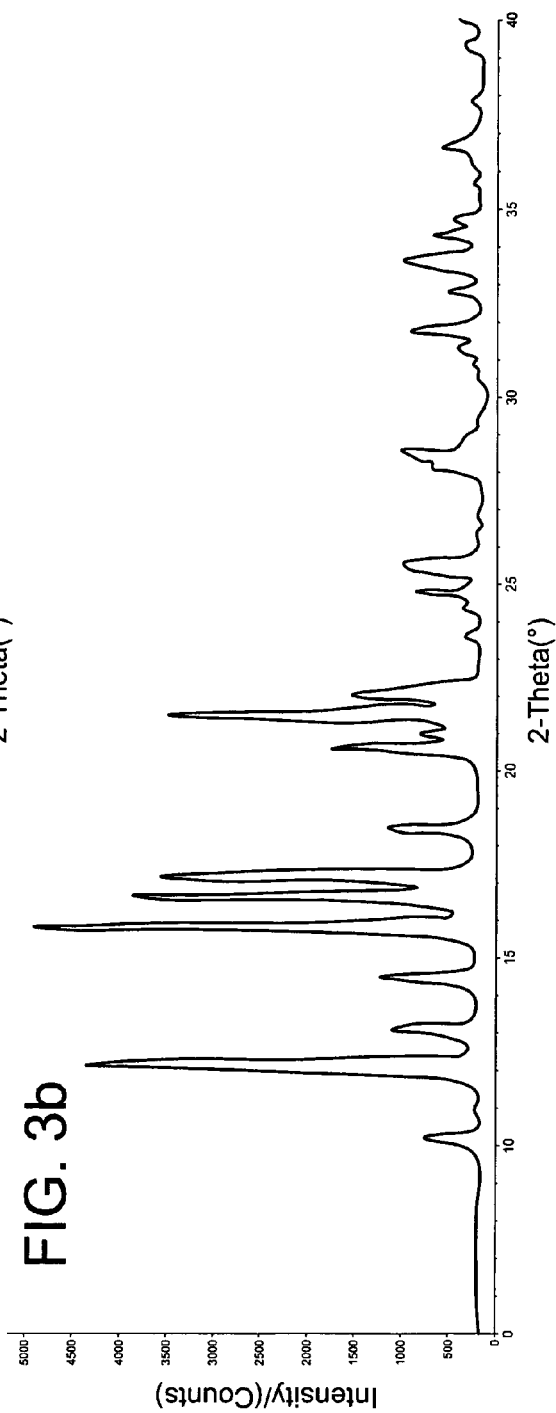

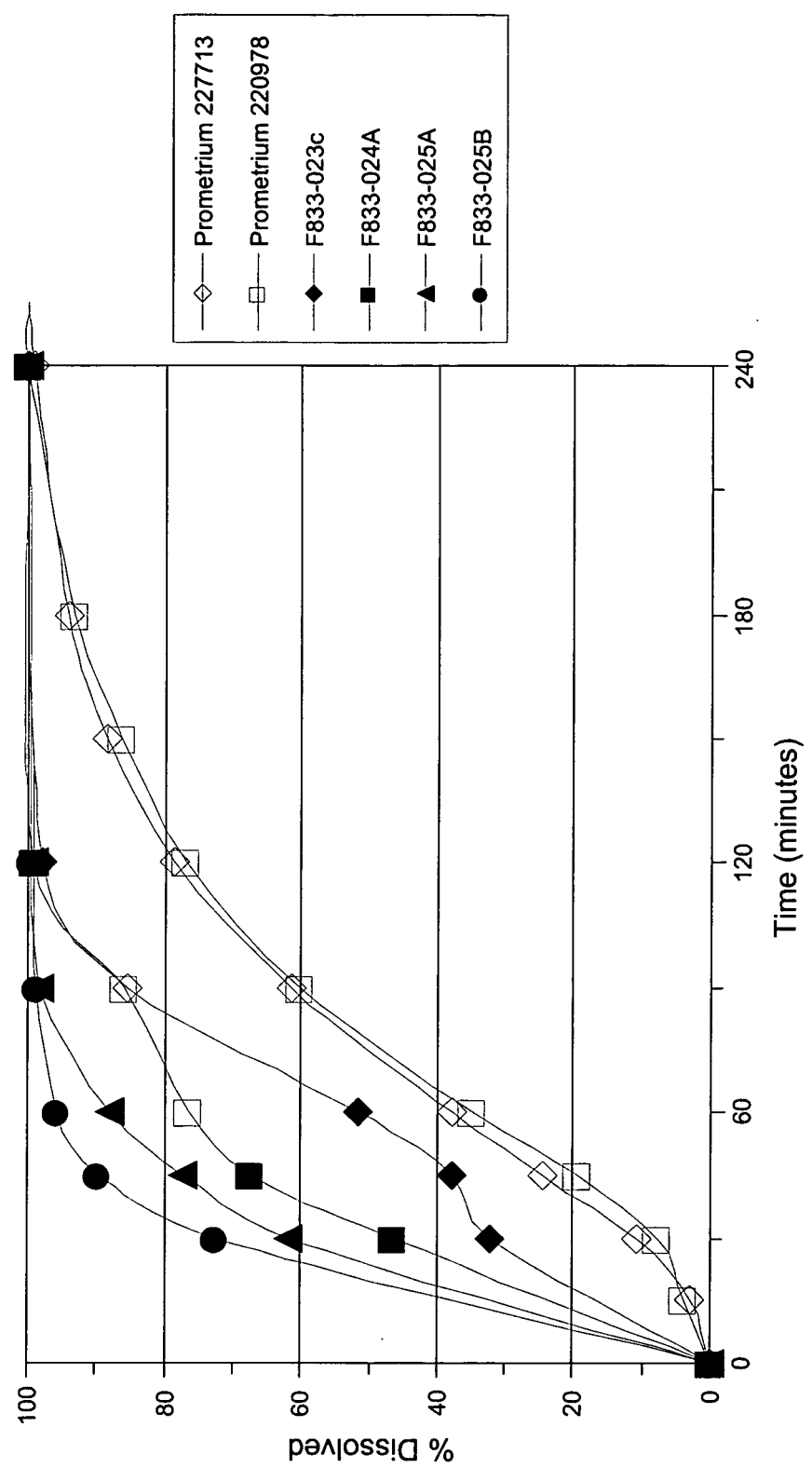

METHOD OF PREPARATION OF MIXED PHASE CO-CRYSTALS WITH ACTIVE AGENTS

CROSS-REFERENCE TO RELATED PATENT APPLICATIONS

This patent application claims the benefit of U.S. Provisional Patent Application No. 60/559,862, filed Apr. 6, 2004 and U.S. Provisional Patent Application No. 60/528,232, filed Dec. 9, 2003, which are incorporated by reference herein.

FIELD OF THE INVENTION

This invention pertains to methods of preparing an active agent as mixed phase co-crystals that have unique physical properties that differ from the active agent in pure form, as well as compositions comprising mixed phase co-crystals. The formulated mixed phase co-crystals are heterogenous and contain crystalline regions within the particles/granules produced. Mixed phase co-crystals are useful for systemic delivery of the active agent as human and animal pharmaceuticals, dietary supplements, and agrochemicals. Furthermore, mixed phase co-crystals have utility in imparting desirable physical and stability properties otherwise not achievable for the pure active agent or in combination as a simple formulation with the materials incorporated with the active agent.

BACKGROUND OF THE INVENTION

Co-crystals occur in nature and form spontaneously with closely related chemical structures, such as chemical isomers (racemates, diasteriomers, and the like). Co-crystals are also found for materials that complex together in solution such as protein-ligands, chelates, inclusion complexes as with cyclodextrins, and ligands. In U.S. Pat. Nos. 4,971,797; 6,312,723 and 6,312,712, complexes of cyclodextrin and active agents are described as being co-crystallized together from solution. These complexes lack the flexibility to incorporate materials with broadly different chemical structures and lack the multi-functional properties that mixed co-crystals can impart.

In certain cases, macromolecules (both polymers and biopolymers) are capable of forming co-crystals with other macromolecules. These co-crystallized products have been used to isolate macromolecules such as proteins for structural characterization. An example of this is found in the paper by Murphy et al. (*Acta Crystallogr D Biol Crystallogr*, 55(Pt 9), 1594-1597 (1999)). These simple co-crystals are not useful to enhance solubility, dissolution or absorption of poorly absorbed active agents.

Minor amounts of materials can be incorporated in a particle sub-structure. These components co-exist with crystalline phases of the particle and produce co-crystalline regions within the particle. The resulting co-crystallized material has a high level of crystallinity and lacks significant amounts of amorphous phase. Examples of these applications can be found in patents describing the dilution of sweetening agents in sugar carriers as in U.S. Pat. Nos. 6,214,402 and 6,365,216. Incorporation of small amounts of single constituents differs from mixed phase co-crystals since the particles produced do not have a significant amount of amorphous phase as indicated by melting properties and solubility. In addition, these materials do not contain an active agent, lack the high concentrations that the mixed phase co-crystals enable, and lack the multi-functional aspects that mixed phase co-crystals offer with respect to improved drug delivery.

Co-crystallization of chemically related materials is illustrated by the preparation of co-crystallized sugars (U.S. Pat. Nos. 4,101,680 and 4,338,339), of acetylenic compounds (U.S. Pat. No. 4,384,980), and sugar alcohols (U.S. Pat. Nos. 5,679,398; 5,958,471 and 6,083,438). The simple co-crystals therein described do not have the broad utility that mixed phase co-crystals have for the enhancement of properties of widely different structures and physico-chemical properties.

Incorporation of minor components by a process described as 'co-crystallization' that yields a product of indeterminate crystalline structure is illustrated by U.S. Pat. Nos. 6,376,481, and 6,267,963 (sterol esters); U.S. Pat. No. 6,214,402 (dilution of sweetener); U.S. Pat. No. 4,751,294 (stabilization by a base); U.S. Pat. No. 5,910,523 (nanocomposites); U.S. Pat. No. 5,876,506 (mesomorphic sugar), U.S. Pat. No. 5,075,291 (uniform dispersion of drug in sugar alcohol); and U.S. Pat. No. 5,451,416. These materials of indeterminate structure lack the ability of mixed phase co-crystals to maintain primary crystalline characteristics of the active agent while imparting amorphous-like properties along with designed functionalities to enhance solubility, dissolution, and absorption.

Complex mixtures of crystalline materials formed by melt/congealing process are described in U.S. Pat. No. 6,267,963 (sterol-emulsion complexes); U.S. Pat. Nos. 4,855,326 and 5,853,762 (rapidly dissolving dosage unit); and U.S. Pat. No. 5,075,291. The process for preparing co-crystals by evaporation or cooling from a solvent system is described in U.S. Pat. No. 4,145,214 (photoconductors); U.S. Pat. Nos. 4,751,294; 4,971,797; and 6,214,402. Applications for which no active agent is incorporated are described in U.S. Pat. Nos. 4,145,214 and 4,384,980. These materials of indeterminate structure lack the ability of mixed phase co-crystals to maintain primary crystalline characteristics of the active agent while imparting amorphous-like properties along with designed functionalities to enhance solubility, dissolution, and absorption.

In the field of active agent delivery, inherent problems associated with the active agent exist, such as particle size, stability, solubility, powder physical properties and release rates. New and improved methods to solve the problems associated with active agent delivery are needed. The invention provides such a method, as well as mixed phase co-crystal compositions comprising an active agent. These and other advantages of the invention, as well as additional inventive features, will be apparent from the description of the invention provided herein.

BRIEF SUMMARY OF THE INVENTION

The invention is directed to a method of preparing mixed phase co-crystals comprising: (a) forming a first solution of a first active agent and at least one crystal lattice modifier dissolved in a solvent; (b) mixing an anti-solvent with the first solution to form a second solution; and (c) forming a mixed phase crystalline material, wherein the active agent and crystal lattice modifier are contained within the mixed phase crystalline material.

The invention also is directed to a mixed phase co-crystal composition comprising a mixed phase co-crystal of an active agent and at least one crystal lattice modifier, wherein the content of the active agent ranges from about 5% to 95% by weight of the total weight of the material, and wherein the crystal lattice modifier ranges from about 2% to 95% by weight for each individual modifier of the total weight of the material.

BRIEF DESCRIPTION OF THE DRAWINGS

FIG. 2B is a graph of an XRD pattern of a mixed phase co-crystal of a crystal lattice modifier (stearic acid) and active agent (hydrocortisone).

FIG. 3A is a graph of an XRD pattern of a mixed phase co-crystal of hydrocortisone (HC) acetate, Methocel E4M (hydroxypropyl methylcellulose), and cetosteryl alchohol.

FIG. 3B is a graph of an XRD pattern of pure HC acetate.

FIG. 6 is a graph showing comparing the in vitro dissolution rate for four lots of mixed phase co-crystal formulations (F833-023c, -024A, -025A, and -025B) containing the active ingredient progesterone as compared to commercial Prometrium 200 mg capsules from two batches.

DETAILED DESCRIPTION OF THE INVENTION

Figure 1A:
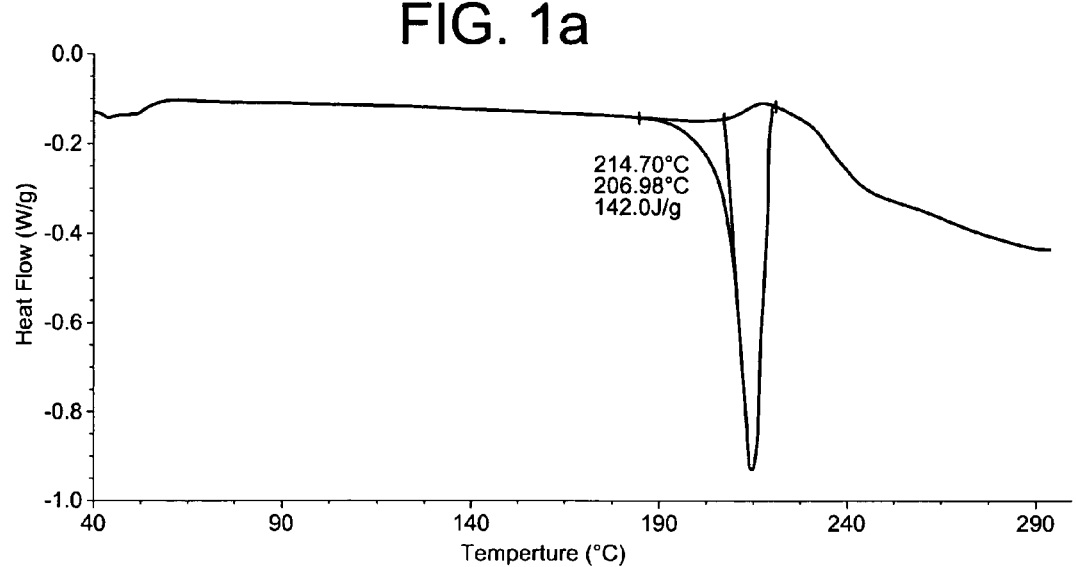
FIG. 1A is a graph showing heat flow to temperature of a pure form of active agent wherein the active agent is hydrocortisone acetate.

The mixed phase co-crystal materials produced by this invention have unique and unexpected properties such as increased apparent solubility, increased dissolution rate, reduced melting point of the active agent, and decrease in crystallinity of the active agent. In addition, the mixed phase co-crystal materials produce supersaturated concentrations of active agent for prolonged periods of time when suspended in water, which facilitates absorption in vivo. These changes in properties of the active agent are particularly advantageous for the delivery of the active agent, e.g., in an oral dosage form.

Furthermore, combinations of more than one crystal lattice modifier with the active agent can result in additive and super-additive effects that cannot be obtained with monotropic co-crystal materials. The enhanced properties of the mixed phase co-crystal materials are obtained even when the thermodynamically favored polymorph of the active agent is present as a component of the mixed phase co-crystal structure. Mixed phase co-crystal materials enable formation of conglomerates of the active agent with modifiers that facilitate drug absorption process through permeability modification, inhibitors of gut wall metabolism, and stabilization of supersaturated solutions. Since these materials are linked through the conglomerated mixed phase co-crystal structure, they act in concert with the dissolution of the active agent and are resistant to premature dissolution of the modifier in the absence of the active agent. By this mechanism the modifier imparts a full effect.

The process herein described for the mixed phase co-crystals is well suited for the direct formation and incorporation of mixed phase co-crystals as part of the dosage form manufacturing process without the need to isolate or purify the mixed phase co-crystal material.

Accordingly, the present invention is directed to mixed phase co-crystal compositions and methods of making mixed phase co-crystal compositions. The inventive method of preparing mixed phase co-crystals comprises: (a) forming a first solution of an active agent and at least one crystal lattice modifier dissolved in a solvent; (b) mixing an anti-solvent with the first solution to form a second solution; and (c) forming the mixed phase co-crystal composition, wherein the active agent and crystal lattice modifier are contained within the mixed phase co-crystal composition. The inventive method can further comprise evaporating the solvent(s), isolating the mixed phase co-crystal composition, washing the mixed phase co-crystal composition, and/or drying the mixed phase co-crystal composition.

A mixed phase co-crystal is a particle or granule composed of two or more crystalline or non-crystalline phases that are distributed randomly throughout the particle structure. One or more of the mixed phase co-crystal components must be solids at room temperature.

An active agent that is co-crystallized with one or more materials (additives) forms a mixed phase co-crystalline form of the active agent and additive(s) that behaves as conglomerated particles or granules that have unique physical properties that are distinguishable from the pure active agent or pure additive(s). These formulated mixed phase co-crystals have crystalline, co-crystalline, and amorphous regions within the particle matrix. The active agent's crystalline form is usually maintained except that the additive(s) are co-crystallized as part of active agent's crystal lattice structure, thus forming co-crystalline regions or amorphous regions or semi-crystalline regions with crystal defects. This results in a characteristic reduction in melting point and crystallinity of the thermodynamically favored crystalline form of the active agent.

Although not wishing to be bound by any particular theory, it is believed that the additive(s) are co-crystallized as minor non-stoichiometric components in the active agent's crystalline matrix. This co-crystalline phase has semi-crystalline nature and contains a high incidence of crystal defects. Any excess additive that is not co-crystallized with the active agent forms a separate phase (Additive Phase) apart from the active agent, which results in the mixed phase co-crystal composition. The Additive Phase and the active agent crystals containing co-crystallized additive can be tightly agglomerated forming a mixed phase co-crystal particle. The unique physical properties obtained by this process of preparation can include changes in apparent solubility, crystallinity, water wetability, dissolution rates, physical powder properties (e.g., bulk density, absolute density, refractive index, x-ray diffraction, spectral, flowability, hygroscopicity, adsorption, and compaction), bioavailability, apparent permeability, apparent taste, and/or stability. For example, the inventive method of preparation of the composition provides (a) an increase in water solubility, (b) a decrease in melting point, (c) decrease in melting enthalpy, (d) an increase in dissolution rate, (e) a reduction in crystallinity, or (f) a combination of two or more of (a)-(e) as compared to the active agent itself.

The mixed phase co-crystal that forms from the active agent and additive(s) is not a pure form stiochiometric eutectic. The mixed phase co-crystal composition produced according to the invention are thermodynamically favored. That is, the crystals exist at a lower energy, stable state.

In another aspect of the invention, after step (b) a kinetically favored crystalline phase is formed in the second solution. The kinetically favored crystalline phase is also characterized as kinetically derived, meta-stable and thermodynamically disfavored. The meta-stable (i.e., kinetically favored) crystalline phase is typically formed as a precipitate in the second solution. The meta-stable crystalline phase is then subsequently transformed (i.e., converted) to the thermodynamically favored mixed-phase co-crystal comopsition. The mixed phase co-crystalline material of the invention are kinetically favored and form upon standing and/or mixing of the initial meta-stable crystalline phase.

The amount of time required to achieve transformation (i.e., conversion) from a kinetically favored crystalline phase to the mixed phase co-crystal composition depends on the particular active agent and other additives present in the second solution. The second solution containing the initial meta-stable crystalline phase is generally mixed or allowed to stand for a sufficient period of time to permit complete conversion to the mixed phase co-crystalline material. This transformation step may take occur for any suitable amount of time (e.g., about 10 seconds, about 30 seconds, about 1 minute, about 5 minutes, about 10 minutes, about 30 minutes, about 1 hour, about 2 hours, about 10 hours, about 20 hours, about 30 hours, about 40 hours, about 50 hours, or more). One of ordinary skill in the art will recognize the amount of time required for conversion of the kinetically favored crystalline material to the thermodynamically favored mixed phase co-crystal composition. Incomplete conversion will result in problems filtering the crystalline material, and therefore, more incubation time is required.

The active agent for use in the composition and method of the invention include any suitable active agent. The active agent is preferably a small chemical entity that is approximately less than 10,000 daltons (e.g., less than about 9,000 daltons, less than about 8,000 daltons, less than about 7,000 daltons, less than about 6,000 daltons, less than about 5,000 daltons), such as a pharmacologically active substance (drug), vitamin, insecticide, fungicide, antibacterial agent, antiviral agent, antiparasitic agent or hormone. Exemplary of active agents include, but are not limited to the following:

1. α-Adrenergic agonists such as Adrafinil, Adrenolone, Amidephrine, Apraclonidine, Budralazine, Clonidine, Cyclopentamine, Detomidine, Dimetofrine, Dipivefrin, Ephedrine, Epinephrine, Fenoxazoline, Guanabenz, Guanfacine, Hydroxyamphetamine, Ibopamine, Indanazoline, Isometheptene, Mephentermine, Metaraminol, Methoxamine Hydrochloride, Methylhexaneamine, Metizolene, Midodrine, Naphazoline, Norepinephrine, Norfenefrine, Octodrine, Octopamine, Oxymetazoline, Phenylephrine Hydrochloride, Phenylpropanolamine Hydrochloride, Phenylpropylmethylamine, Pholedrine, Propylhexedrine, Pseudoephedrine, Rilmenidine, Synephrine, Tetrahydrozoline, Tiamenidine, Tramazoline, Tuaminoheptane, Tymazoline, Tyramine, and Xylometazoline.

2. β-Adrenergic agonists such as Albuterol, Bambuterol, Bitolterol, Carbuterol, Clenbuterol, Clorprenaline, Denopamine, Dioxethedrine, Dopexamine, Ephedrine, Epinephrine, Etafedrine, Ethylnorepinephrine, Fenoterol, Formoterol, Hexoprenaline, Ibopamine, Isoetharine, Isoproterenal, Mabuterol, Metaproterenol, Methoxyphenamine, Oxyfedrine, Pirbuterol, Prenalterol, Procaterol, Protokylol, Reproterol, Rimiterol, Ritodrine, Soterenol, Terbuterol, and Xamoterol.

3. α-Adrenergic blockers such as Amosulalol, Arotinolol, Dapiprazole, Doxazosin, Ergoloid Mesylates, Fenspiride, Indoramin, Labetalol, Nicergoline, Prazosin, Terazosin, Tolazoline, Trimazosin and Yohimbine.

4. β-Adrenergic blockers such as Acebutolol, Alprenolol, Amosulalol, Arotinolol, Atenolol, Befunolol, Betaxolol, Bevantolol, Bisoprolol, Bopindolol, Bucumolol, Befetolol, Bufuralol, Bunitrolol, Bupranolol, Butidrine Hydrochloride, Butofilolol, Carazolol, Carteolol, Carvedilol, Celiprolol, Cetamolol, Cloranolol, Dilevalol, Epanolol, Esmolol, Indenolol, Labetalol, Levobunolol, Mepindolol, Metipranalol, Metoprolol, Moprolol, Nadoxolol, Nifenalol, Nipradilol, Oxprenolol, Penbutolol, Pindolol, Practolol, Pronethalol, Propranolol, Sotalol, Sulfinalol, Talinolol, Tertatolol, Timolol, Toliprolol, and Xibenolol.

5. Alcohol deterrents such as Calcium Cyanamide Citrated, Disulfiram, Nadide, and Nitrefazole.

6. Aldose reductase inhibitors such as Epalrestat, Ponalrestat, Sorbinil, and Tolrestat.

7. Anabolics such as Androisoxazole, Androstenediol, Bolandiol, Bolasterone, Clostebol, Ethylestrenol. Formyldienolone, 4-Hydroxy-19-nortestosterone, Methandriol, Methenolone, Methyltrienolone, Nandrolone, Nandrolone Decanoate, Nandrolone p-Hexyloxyphenylpropionate, Nandrolone Phenpropionate, Norbolethone, Oxymesterone, Pizotyline, Quinbolone, Stenbolone, and Trenbolone.

8. Analgesics (narcotic) such as Alfentanil, Allylprodine, Alphaprodine, Anileridine, Benzylmorphine, Bezitramide, Buprenorphine, Butorphanol, Clonitazene, Codeine, Codeine Methyl Bromide, Codeine Phosphate, Codeine Sulfate, Desomorphine, Dextromoramide, Dezocine, Diampromide, Dihydrocodeine, Dihydrocodeinone Enol Acetate, Dihydromorphine, Dimenoxadol, Dimepheptanol, Dimethylthiambutene, Dioxaphetyl Butyrate, Dipipanone, Eptazocine, Ethoheptazine, Ethylmethlythiambutene, Ethylmorphine, Etonitazene, Fentanyl, Hydrocodone, Hydromorphone, Hydroxypethidine, Isomethadone, Ketobemidone, Levorphanol, Lofentanil, Meperidine, Meptazinol, Metazocine, Methadone Hydrochloride, Metopon, Morphine, Morphine Derivatives, Myrophine, Nalbuphine, Narceine, Nicomorphine, Norlevorphanol, Normethadone, Normorphine, Norpipanone, Opium, Oxycodone, Oxymorphone, Papaveretum, Pentazocine, Phenadoxone, Phenazocine, Pheoperidine, Piminodine, Piritramide, Proheptazine, Promedol, Properidine, Propiram, Propoxyphene, Sufentanil, and Tilidine.

9. Analgesics (non-narcotic) such as Acetaminophen, Acetaminosalol, Acetanilide, Acetylsalicylsalicylic Acid, Alclofenac, Alminoprofen, Aloxiprin, Aluminum Bis(acetylsalicylate), Aminochlorthenoxazin, 2-Amino-4-picoline, Aminopropylon, Aminopyrine, Ammonium Salicylate, Antipyrine, Antipyrine Salicylate, Antrafenine, Apazone, Aspirin, Benorylate, Benoxaprofen, Benzpiperylon, Benzydamine, p-Bromoacetanilide, 5-Bromosalicylic Acid Acetate, Bucetin, Bufexamac, Bumadizon, Butacetin, Calcium Acetylsalicylate, Carbamazepine, Carbetidine, Carbiphene, Carsalam, Chloralantipyrine, Chlorthenoxazin(e), Choline Salicylate, Cinchophen, Ciramadol, Clometacin, Cropropamide, Crotethamide, Dexoxadrol, Difenamizole, Diflunisal, Dihydroxyaluminum Acetylsalicylate, Dipyrocetyl, Dipyrone, Emorfazone, Enfenamic Acid, Epirizole, Etersalate, Ethenzamide, Ethoxazene, Etodolac, Felbinac, Fenoprofen, Floctafenine, Flufenamic Acid, Fluoresone, Flupirtine, Fluproquazone, Flurbiprofen, Fosfosal, Gentisic Acid, Glafenine, Ibufenac, Imidazole Salicylate, Indomethacin, Indoprofen, Isofezolac, Isoladol, Isonixin, Ketoprofen, Ketorolac, p-Lactophenetide, Lefetamine, Loxoprofen, Lysine Acetylsalicylate, Magnesium Acetylsalicylate, Methotrimeprazine, Metofoline, Miroprofen, Morazone, Morpholine Salicylate, Naproxen, Nefopam, Nifenazone, 5' Nitro-2' propoxyacetanilide, Parsalmide, Perisoxal, Phenacetin, Phenazopyridine Hydrochloride, Phenocoll, Phenopyrazone, Phenyl Acetylsalicylate, Phenyl Salicylate, Phenyramidol, Pipebuzone, Piperylone, Prodilidine, Propacetamol, Propyphenazone, Proxazole, Quinine Salicylate, Ramifenazone, Rimazolium Metilsulfate, Salacetamide, Salicin, Salicylamide, Salicylamide O-Acetic Acid, Salicylsulfuric Acid, Salsalte, Salverine, Simetride, Sodium Salicylate, Sulfamipyrine, Suprofen, Talniflumate, Tenoxicam, Terofenamate, Tetradrine, Tinoridine, Tolfenamic Acid, Tolpronine, Tramadol, Viminol, Xenbucin, and Zomepirac.

10. Androgens such as Boldenone, Fluoxymesterone, Mestanolone, Mesterolone, Methandrostenolone, 17-Methyltestosterone, Methyltestosterone, 17α-Methyltestosterone 3-Cyclopentyl Enol Ether, Norethandrolone, Normethandrone, Oxandrolone, Oxymesterone, Oxymetholone, Prasterone, Stanlolone, Stanozolol, Testosterone, Testosterone 17-Chloral Hemiacetal, Testosterone 17β-Cypionate, Testosterone Enanthate, Testosterone Nicotinate, Testosterone Pheynylacetate, Testosterone Propionate, and Tiomesterone.

11. Anesthetics (intravenous) such as Acetamidoeugenol, Alfadolone Acetate, Alfaxalone, Amucaine, Amolanone, Amylocaine Hydrochloride, Benoxinate, Betoxycaine, Biphenamine, Bupivacaine, Butacaine, Butaben, Butanilicaine, Burethamine, Buthalital Sodium, Butoxycaine, Carticaine, 2-Chloroprocaine Hydrochloride, Cocaethylene, Cocaine, Cyclomethycaine, DibucaineHydrochloride, Dimethisoquin, Dimethocaine, Diperadon Hydrochloride, Dyclonine, Ecgonidine, Ecgonine, Ethyl Aminobenzoate, Ethyl Chloride, Etidocaine, Etoxadrol, β-Eucaine, Euprocin, Fenalcomine, Fomocaine, Hexobarbital, Hexylcaine Hydrochloride, Hydroxydione Sodium, Hydroxyprocaine, Hydroxytetracaine, Isobutyl p-Aminobenzoate, Kentamine, Leucinocaine Mesylate, Levoxadrol, Lidocaine, Mepivacaine, Meprylcaine Hydrochloride, Metabutoxycaine Hydrochloride, Methohexital Sodium, Methyl Chloride, Midazolam, Myrtecaine, Naepaine, Octacaine, Orthocaine, Oxethazaine, Parethoxycaine, Phenacaine Hydrochloride, Phencyclidine, Phenol, Piperocaine, Piridocaine, Polidocanol, Pramoxine, Prilocaine, Procaine, Propanidid, Propanocaine, Proparacaine, Propipocaine, Propofol, Propoxycaine Hydrochloride, Pseudococaine, Pyrrocaine, Quinine Urea Hydochloride, Risocaine, Salicyl Alcohol, Tetracaine Hydrochloride, Thialbarbital, Thimylal, Thiobutabarbital, Thiopental Sodium, Tolycaine, Trimecaine, and Zolamine.

12. Anorectics such as Aminorex, Amphecloral, Amphetamine, Benzaphetamine, Chlorphentermine, Clobenzorex, Cloforex, Clortermine, Cyclexedrine, Destroamphetamine Sulfate, Diethylpropion, Diphemethoxidine, N-Ethylamphetamine, Fenbutrazate, Fenfluramine, Fenproporex, Furfuirylmethylamphetamine, Levophacetoperate, Mazindol, Mefenorex, Metamfeproamone, Methamphetamine, Norpseudoephedrine, Phendimetrazine, Phenmetrazine, Phenpentermine, Phenylpropanolamine Hydrochloride, and Picilorex.

13. Anthelmintics (Cestodes) such as Arecoline, Aspidin, Aspidinol, Dichlorophen(e), Embelin, Kosin, Napthalene, Niclosamide, Pellertierine, Pellertierine Tannate, and Quinacrine.

14. Anthelmintics (Nematodes) such as Alantolactone, Amoscanate, Ascaridole, Bephenium, Bitoscanate, Carbon Tetrachloride, Carvacrol, Cyclobendazole, Diethylcarbamazine, Diphenane, Dithiazanine Iodide, Dymanthine, Gentian Violet, 4-Hexylresorcinol, Kainic Acid, Mebendazole, 2-Napthol, Oxantel, Papain, Piperazine, Piperazine Adipate, Piperazine Citrate, Piperazine Edetate Calcium, Piperazine Tartrate, Pyrantel, Pyrvinium Pamoate, α-Santonin, Stilbazium Iodide, Tetrachloroethylene, Tetramisole, thiabendazole, Thymol, Thymyl N-Isoamylcarbamate, Triclofenol Piperazine, and Urea Stibamine.

15. Anthelmintics (Onchocerca) such as Ivermectin and Suramin Sodium.

16. Anthelmintics (Schistosoma) such as Amoscanate, Amphotalide, Antimony Potassium Tartrate, Antimony Sodium Gluconate, Antimony Sodium Tartrate, Antimony Sodium Thioglycollate, Antimony Thioglycollamide, Becanthone, Hycanthone, Lucanthone Hydrochloride, Niridazole, Oxamniquine, Praziquantel, Stibocaptate, Stibophen, and Urea Stibamine.

17. Anthelmintic (Trematodes) such as Anthiolimine and Tetrachloroethylene.

18. Antiacne drugs such as Algestone Acetophenide, Azelaic Acid, Benzoyl Peroxide, Cyoctol, Cyproterone, Motretinide, Resorcinol, Retinoic Acid, and Tetroquinone.

19. Antiallergics such as Amlexanox, Astemizole, Azelastine, Cromolyn, Fenpiprane, Histamine, Ibudilast, Nedocromil, Oxatomide, Pentigetide, Poison Ivy Extract, Poison Oak Extract, Poison Sumac Extract, Repirinast, Tranilast, Traxanox, and Urushiol.

20. Antiamebics such as Arsthinol, Bialamnicol, Carbarsone, Cephaeline, Chlorbetamide, Chloroquine, Chlorphenoxamide, Chlortetracycline, Dehydroemetine, Dibromopropamidine, Diloxanide, Dephetarsone, Emetine, Fumagillin, Glaucarubin, Glycobiarsol, 8-Hydroxy-7-iodo-5-quinolinesulfonic Acid, Iodochlorhydroxyquin, Iodoquinol, Paromomycin, Phanquinone, Phearsone Sulfoxylate, Polybenzarsol, Propamidine, Quinfamide, Secnidazole, Sulfarside, Teclozan, Tetracycline, Thiocarbamizine, Thiocarbarsone, and Tinidazole.

21. Antiandrogens such as Bifluranol, Cyoctol, Cyproterone, Delmadinone Acetate, Flutimide, Nilutamide, and Oxendolone.

22. Antianginals such as Acebutolol, Alprenolol, Amiodarone, Amlodipine, Arotinolol, Atenolol, Bepridil, Bevantolol, Bucumolol, Bufetolol, Bufuralol, Bunitrolol, Bupranolol, Carozolol, Carteolol, Carvedilol, Celiprolol, Cinepazet Maleate, Diltiazem, Epanolol, Felodipine, Gallopamil, Imolamine, Indenolol, Isosorbide Dinitrate, Isradipine, Limaprost, Mepindolol, Metoprolol, Molsidomine, Nadolol, Nicardipine, Nifedipine, Nifenalol, Nilvadipine, Nipradilol, Nisoldipine, Nitroglycerin, Oxprenolol, Oxyfedrine, Ozagrel, Penbutolol, Pentaerythritol Tetranitrate, Pindolol, Pronethalol, Propranolol, Sotaiol, Terodiline, Timolol, Toliprolol, and Verapamil.

23. Antiarrhythmics such as Acebutol, Acecaine, Adenosine, Ajmaline, Alprenolol, Amiodarone, Amoproxan, Aprindine, Arotinolol, Atenolol, Bevantolol, Bretylium Tosylate, Bubumolol, Bufetolol, Bunaftine, Bunitrolol, Bupranolol, Butidrine Hydrochloride, Butobendine, Capobenic Acid, Carazolol, Carteolol, Cifenline, Cloranolol, Disopyramide, Encainide, Esmolol, Flecainide, Gallopamil, Hydroquinidine, Indecainide, Indenolol, Ipratropium Bromide, Lidocaine, Lorajmine, Lorcainide, Meobentine, Metipranolol, Mexiletine, Moricizine, Nadoxolol, Nifenalol, Oxprenolol, Penbutolol, Pindolol, Pirmenol, Practolol, Prajmaline, Procainamide Hydrochloride, Pronethalol, Propafenone, Propranolol, Pyrinoline, Quinidine Sulfate, Quinidine, Sotalol, Talinolol, Timolol, Tocainide, Verapamil, Viquidil, and Xibenolol.

24. Antiarteriosclerotics such as Pyridinol Carbamate.

25. Antiarthritic/Antirheumatics such as Allocupreide Sodium, Auranofin, Aurothioglucose, Aurothioglycanide, Azathioprine, Calcium 3-Aurothio-2-propanol-1-sulfonate, Chloroquine, Clobuzarit, Cuproxoline, Diacerein, Glucosamine, Gold Sodium Thiomalate, Gold Sodium Thiosulfate, Hydroxychloroquine, Kebuzone, Lobenzarit, Melittin, Methotrexate, Myoral, and Penicillamine.

26. Antibacterial (antibiotic) drugs including Aminoglycosides such as Amikacin, Apramycln, Arbekacin, Bambermycins, Butirosin, Dibekacin, Dihdrostreptomycin, Fortimicin(s), Gentamicin, Ispamicin, Kanamycin, Micronomicin, Neomycin, Neomycin Undecylenate, Netilmicin, Paromomycin, Ribostamycin, Sisomicin, Spectinomycin, Streptomycin, Streptonicozid, and Tobramycin; Amphenicols such as Azidamfenicol, Chloramphenicol, Chloramphenicol Palmitate, Chloramphenicol Pantothenate, Florfenicol, and Thiamphenicol; Ansamycins such as Rifamide, Rifampin, Rifamycin, and Rifaximin; β-Lactams, including: Carbapenems such as Imipenem; Cephalosporins such as Cefactor, Cefadroxil, Cefamandole, Cefatrizine, Cefazedone, Cefazolin, Cefixime, Cefmenoxime, Cefodizime, Cefonicid, Cefoperazone, Ceforanide, Cefotaxime, Cefotiam, Cefpimizole, Cefpirimide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridie, Cephalosporin, Cephalothin, Cephapirin Sodium, Cephradine and Pivcefalexin; Cephamycins such as Cefbuperazone, Cefmetazole, Cefminox, Cefetan and Cefoxitin; Monobactams such as Aztreonam, Carumonam and Tigemonam; Oxacephems such as Flomoxef and Moxolactam; Penicillins such as Amidinocillin, Amdinocillin Pivoxil, Amoxicillin, Ampicillan, Apalcillin, Aspoxicillin, Azidocillan, Azlocillan, Bacampicillin, Benzylpenicillinic Acid, Benzylpenicillin Sodium, Carbenicillin, Carfecillin Sodium, Carindacillin, Clometocillin, Cloxacillin, Cyclacillin, Dicloxacillin, Diphenicillin Sodium, Epicillin, Fenbenicillin, Floxicillin, Hetacillin, Lenampicillin, Metampicillin, Methicillin Sodium, Mezlocillin, Nafcillin Sodium, Oxacillin, Penamecillin, Penethamate Hydriodide, Penicillin G Benethamine, Penicillin G Benzathine, Penicillin G Benzhydrylamine, Penicillin G Calcium, Penicillin G Hydrabamine, Penicillin G Potassium, Penicillin G Procaine, Penicillen N, Penicillin O, Penicillin V, Penicillin V Benzathine, Penicillin V Hydrabamine, Penimepicycline, Phenethicillin Potassium, Piperacillin, Pivapicillin, Propicillin, Quinacillin, Sulbenicillin, Talampicillin, Temocillin and Ticarcillin; Lincosamides such as Clindamycin and Lincomycin; Macrolides such as Azithromycin, Carbomycin, Clarithromycin, Erythromycin, Erythromycin Acistrate, Erythromycin Estolate, Erythromycin Glucoheptonate, Erythromycin Lactobionate, Erythromycin Propionate, Erythromycin Stearate, Josamycin, Leucomycins, Midecamycins, Miokamycin, Oleandomycin, Primycin, Rokitamycin, Rosaramicin, Roxithromycin, Spiramycin and Troleandomycin; Polypeptides such as Amphomycin, Bacitracin, Capreomycin, Colistin, Enduracidin, Enviomycin, Fusafumgine, Gramicidin(s), Gramicidin S, Mikamycin, Polymyxin, Polymyxin B-Methanesulfonic Acid, Pristinamycin, Ristocetin, Teicoplanin, Thiostrepton, Tuberactinomycin, Tyrocidine, Tyrothricin, Vancomycin, Viomycin, Viomycin Pantothenate, Virginiamycin and Zinc Bacitracin; Tetracyclines such as Apicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Senociclin and Tetracycline; and other antibiotics such as Cycloserine, Mupirocin and Tuberin.

27. Antibacterial drugs (synthetic), including: 2,4-Diaminopyrimidines such as Brodimoprim, Tetroxoprim and Trimethoprim; Nitrofurans such as Furaltadone, Furazolium Chloride, Nifuradene, Nifuratel, Nifurfoline, Nifurpirinol, Nifurprazine, Nifurtoinol and Nitrofurantoin; Quinolones and Analogs such as Amifloxacin, Cinoxacin, Ciprofloxacin, Difloxacin, Enoxacin, Fleroxacin, Flumequine, nomefloxacin, Miloxacin, Nalidixic Acid, Norfloxacin, Ofloxacin, Oxolinic Acid, Pefloxacin, Pipemidic Acid, Piromidic Acid, Rosoxacin, Temafloxacin and Tosufloxacin; Sulfonamides such as Acetyl Sulfamethoxypyrazine, Acetyl Sulfisoxazole, Azosulfamide, Benzylsulfamide, Chloramine-B, Chloramine-T, Dichloramine T, Formosulfathiazole, N.sup.2 Formylsulfisomidine, N.sup.2-β-D-Glucosylsulfanilamide, Mafenide, 4'-(Methylsulfamoyl) sulfanilanilide, p-Nitrosulfathiazole, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, Sulfamidochrysoidine. Sulfamoxole, Sulfanilamide, Sulfanilamidomethanesulfonic Acid Triethanolamine Salt, 4-Sulfanilamidosalicylic Acid, N.sup.4-Sulfanilylsulfanilamide, Sulfanilylurea, N-Sulfanilyl-3,4-xylamide, Sulfanitran, Sulfaperine, Sulfaphenazole. Sulfaproxyline, Sulfapyrazine, Sulfapyridine, Sulfasomizole, Sulfasymazine, Sulfathiazole, Sulfathiourea, Sulfatolamide, Sulfisomidine and Sulfisoxazole; Sulfones such as Acedapsone, Acediasulfone, Acetosulfone Sodium, Dapsone, Diathymosulfone, Glucosulfone Sodium, Solasulfone, Succisulfone, Sulfanilic Acid, p-Sulfanilylbenzylamine, p,p'-Sulfonyldianiline-N.N' digalactoside, Sulfoxone Sodium and Thiazolsulfone; and others such as Clofoctol, Hexedine, Methenamine, Methenamine Anhydromethylenecitrate, Methenamine Hippurate, Methenamine Mandelate, Methenamine Sulfosalicylate, Nitroxoline and Xibomol.

28. Anticholinergics such as Adiphenine Hydrochloride, Alverine, Ambutonomium Bromide, Aminopentamide, Amixetrine, Amprotropine Phosphate, Anisotropine Methylbromide, Apoatropine, Atropine, Atropine N-Oxide, Benactyzine, Benapryzine, Benzetimide, Benzilonium Bromide, Benztropine Mesylate, Bevonium Methyl Sulfate, Biperiden, Butropium Bromide, N-Butylscopolammonium Bromide, Buzepide, Camylofine, Caramiphen Hydrochloride, Chlorbenzoxamine, Chlorphenoxamine, Cimetropium Bromide, Clidinium Bromide, Cyclodrine, Cyclonium Iodide, Cycrimine Hydrochloride, Deptropine, Dexetimide, Dibutoline Sulfate, Dicyclomine Hydrochloride, Diethazine, Difemerine, Dihexyverine, Diphemanil Methylsulfate, N-(1, 2-Diphenylethyl) nicotinamide, Dipiproverine, Diponium Bromide, Emepronium Bromide, Endobenzyline Bromide, Ethopropazine, Ethybenztropine, Ethylbenzhydramine, Etomidoline, Eucatropine, Fenpiverinium Bromide, Fentonium Bromide, Flutropium Bromide, Glycopyrrolate, Heteronium Bromide, Hexocyclium Methyl Sulfate, Homatropine, Hyoscyamine, Ipratropium Bromide, Isopropamide, Levomepate, Mecloxamine, Mepenzolate Bromide, Metcaraphen, Methantheline Bromide, Methixene, Methscopolamine Bromide, Octamylamine, Oxybutynin Chloride, Oxyphencyclimine, Oxyphenonium Bromide, Pentapiperide, Penthienate Bromide, Phencarbamide, Phenglutarimide, Pipenzolate Bromide, Piperidolate, Piperilate, Poldine Methysulfate, Pridinol, Prifinium Bromide, Procyclidine, Propanthel ine Bromide, Propenzolate, Propyromazine, Scopolamine, Scopolamine N-Oxide, Stilonium Iodide, Stramonium, Sultroponium, Thihexinol, Thiphenamil, Tiemonium Iodide, Timepidium Bromide, Tiquizium Bromide, Tridihexethyl Iodide, Trihexyphenidyl Hydrochloride, Tropacine, Tropenzile, Tropicamide, Trospium Chloride, Valethamate Bromide and Xenytropium Bromide.

29. Anticonvulsants such as Acetylpheneturide, Albutoin, Aloxidone, Aminoglutethimide, 4-Amino-3-hydroxybutyric Acid, Atrolactamide, Beclamide, Buramate, Calcium Bromide, Carbamazepine, Cinromide, Clomethiazole, Clonazepam, Decimemide, Diethadione, Dimethadione, Doxenitoin, Eterobarb, Ethadione, Ethosuximide, Ethotoin, Fluoresone, 5-Hydroxytryptophan, Lamotrigine, Magnesium Bromide, Magnesium Sulfate, Mephenytoin, Mephobarbital, Metharbital, Methetoin, Methsuximide, 5-Methyl-5-(3-phenanthryl)hydantoin, 3-Methyl-5-phenylhydantoin, Narcobarbital, Nimetazepam, Nitrazepam, Paramethadione, Phenacemide, Phenetharbital, Pheneturide, Phenobarbital, Phenobarbital Sodium, Phensuximide, Phenylmethylbarbituric Acid, Phenytoin, Phethenylate Sodium, Potassium Bromide, Primidone, Progabide, Sodium Bromide, Solanum, Strontium Bromide, Suclofenide, Sulthiame, Tetrantoin, Trimethadione, Valproic Acid, Valpromide, Vigabatrin and Zonisamide.

30. Antidepressants, including: Bicyclics such as Binedaline, Caroxazone, Citalopram, Dimethazan, Indalpine, Fencamine, Indeloxazine Hydrochcloride, Nefopam, Nomifensine, Oxitriptan, Oxypertine, Paroxetine, Sertraline, Thiazesim, Trazodone and Zometapine; Hydrazides/Hydrazines such as Benmoxine, Iproclozide, Iproniazid, Isocarboxazid, Nialamide, Octamoxin and Phenelzine; Pyrrolidones such as Cotinine, Rolicyprine and Rolipram; Tetracyclics such as Maprotiline, Metralindole, Mianserin and Oxaprotiline. Tricyclics such as Adinazolam, Amitriptyline, Amitriptylinoxide, Amoxapine, Butriptyline, Clomipramine, Demexiptiline, Desipramine, Dibenzepin, Dimetracrine, Dothiepin, Doxepin, Fluacizine, Imipramine, Imipramine N-Oxide, Iprindole, Lofepramine, Melitracen, Metapramine, Nortriptyline, Noxiptilin, Opipramol, Pizotyline, Propizepine, Protriptyline, Quinupramine, Tianeptine and Trimipramine; and others such as Adrafinil, Benactyzine. Bupropion, Butacetin, Deanol, Deanol Aceglumate, Deanol Acetamidobenzoate, Dioxadrol, Etoperidone, Febarbamate, Femoxetine, Fenpentadiol, Fluoxetine, Fluvoxamine, Hematoporphyrin, Hypercinin, Levophacetoperane, Medifoxamine, Minaprine, Moclobemide, Oxaflozane, Piberaline, Prolintane, Pyrisuccideanol, Rubidium Chloride, Sulpiride, Sultopride, Teniloxazine, Thozalinone, Tofenacin, Toloxatone, Tranylcypromine, L-Tryptophan, Viloxazine and Zimeldine.

31. Antidiabetics, including: Biguanides such as Buformin, Metformin and Phenformin; Hormones such as Glucagon, Insulin, Insulin Injection, Insulin Zinc Suspension, Isophane Insulin Suspension, Protamine Zinc Insulin Suspension and Zinc Insulin Crystals; Sulfonylurea derivatives such as Acetohexamide, 1-Butyl-3-metanilylurea, Carbutamide, Chlorpropamide, Glibornuride, Gliclazide, Glipizide, Gliquidone, Glisoxepid, Glyburide, Glybuthiazol (e), Glybuzole, Glyhexamide, Glymidine, Glypinamide, Phenbutamide, Tolazamide, Tolbutamide and Tolcyclamide; and others such as Acarbose, Calcium Mesoxalate and Miglitol.

32. Antidiarrheal drugs such as Acetyltannic Acid, Albumin Tannate, Alkofanone, Aluminum Salicylates-Basic, Catechin, Difenoxin, Diphenoxylate, Lidamidine, Loperamide, Mebiquine, Trillium and Uzarin.

33. Antidiuretics such as Desmopressin, Felypressin, Lypressin, Ornipressin, Oxycinchophen, Pituitary-Posterior, Terlipressin and Vasopressin.

34. Antiestrogens such as Delmadinone Acetate, Ethamoxytriphetol, Tamoxifen and Toremifene.

35. Antifungal drugs (antibiotics), including: Polyenes such as Amphotericin-B, Candicidin, Dermostatin, Filipin, Fungichromin, Hachimycin, Hamycin, Lucensomycin, Mepartricin, Natamycin, Nystatin, Pecilocin and Perimycin; and others such as Azaserine, Griseofulvin, Oligomycins, Neomycin Undecylenate, Pyrrolnitrin, Siccanin, Tubercidin and Viridin.

36. Antifungal drugs (synthetic), including: Allylamines such as Naftifine and Terbinafine; Imidazoles such as Bifonazole, Butoconazole, Chlordantoin, Chlormidazole, Cloconazole, Clotrimazole, Econazole, Enilconazole, Fenticonazole, Isoconazole, Ketoconazole, Miconazole, Omoconazole, Oxiconazole, Nitrate, Sulconazole and Tioconazole; Triazoles such as Fluconazole, Itraconazole and Terconazole; and others such as Acrisorcin, Amorolfine, Biphenamine, Bromosalicylchloranilide, Buclosamide, Calcium Propionate, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Tolciclate, Tolindate, Tolnaftate, Tricetin, Ujothion, Undecylenic Acid and Zinc Propionate.

37. Antiglaucoma drugs such as Acetazolamide, Beflnolol, Betaxolol, Bupranolol, Carteolol, Dapiprazoke, Dichlorphenamide, Dipivefrin, Epinephrine, Levobunolol, Methazolamide, Metipranolol, Pilocarpine, Pindolol and Timolol.

38. Antigonadotropins such as Danazol, Gestrinone and Paroxypropione.

39. Antigout drugs such as Allopurinol, Carprofen, Colchicine, Probenecid and Sulfinpyrazone.

40. Antihistamines, including: Alkylamine derivatives such as Acrivastine, Bamipine, Brompheniramine, Chlorpheniramine, Dimethindene, Metton S., Pheniramine, Pyrrobutamine, Thenaldine, Tolpropamine and Triprolidine; Aminoalkyl ethers such as Bietanautine, Bromodiphenhydramine, Carbinoxamine, Clemastine, Diphenlypyraline, Doxylamine, Embrammine, Medrylamine, Mephenphydramine, p-Methyldiphenhydramine, Orphenadrine, Phenyltoloxamine, Piprinhydrinate and Setasine; Ethylenediamine derivatives such as Alloclamide, p-Bromtripelennamine, Chloropyramine, Chlorothen, Histapyrrodine, Methafurylene, Methaphenilene, Methapyrilene, Phenbenzamine, Pyrilamine, Talastine, Thenyldiamine, Thonzylamine Hydrochloride, Tripelennamine and Zolamine; Piperazines such as Cetirizine, Chlorcyclizine, Cinnarizine, Clocinizine and Hydroxyzine; Tricyclics, including: Phenothiazines such as Ahistan, Etymemazine, Hydroxyazine, N-Hydroxyethylpromethazine Chloride, Isopromethazine, Mequitazine, Promethazine, Pyrathiazine and Thiazinamium Methyl Sulfate; and others such as Azatadine, Clobenzepam, Cyproheptadine, Deptropine, Isothipendyl, Loratadine and Prothipendyl; and other antihistamines such as Antazoline, Astemizole, Azelastine, Cetoxime, Clemizole, Clobenztropine, Diphenazoline, Diphenhydramine, Mebhydroline, Phenindamine, Terfenadine and Tritoqualine.

41. Antihyperlipoproteinemics, including: Aryloxyalkanoic acid derivatives such as Beclorbrate, Bazafibrate, Binifibrate, Ciprofibrate, Clinofibrate, Clofibrate, Clofibric Acid, Etonfibrate, Fenofibrate, Gemfibrozil, Nicofibrate, Pirifibrate, Ronifibrate, Simfibrate and Theofibrate; Bile acid sequesterants such as Cholestyramine Resin, Colestipol and Polidexide; HMG CoA reductase inhibitors such as Lovastatin, Pravastatin Sodium and Simvastatin; Nicotinic acid derivatives Aluminum Nicotinate, Acipimox, Niceritrol, Nicoclonate, Nicomol and Oxiniacic Acid; Thyroid hormones and analogs such as Etiroxate, Thyropropic Acid and Thyroxine; and others such as Acifran, Azacosterol, Benfluorex, β-Benzalbutyramide, Camitine, Chondroitin Sulfate, Clomestone, Detaxtran, Dextran Sulfate Sodium, 5,8,11,14,17-Eicosapentaenoic Acid, Eritadenine, Furazbol, Meglutol, Melinamide, Mytatrienediol, Omithine, γ-Oryzanol, Pantethine, Penataerythritol Tetraacetate, α-Phenylbutyramide, Pirozadil, Probucol, α-Sitosterol, Sultosilic Acid, Piperazine Salt, Tiadenol, Triparanol and Xenbucin.

42. Antihypertensive drugs, including: Arylethanolamine derivatives such as Amosulalol, Bufuralol, Dilevalol, Labetalol, Pronethalol, Sotalol and Sulfinalol; Aryloxypropanolamine derivatives such as Acebutolol, Alprenolol, Arotinolol, Atenolol, Betaxolol, Bevantolol, Bisoprolol, Bopindolol, Bunitrolol, Bupranolol, Butofilolol, Carazolol, Cartezolol, Carvedilol, Celiprolol, Cetamolol, Epanolol, Indenolol, Mepindolol, Metipranolol, Metoprolol, Moprolol, Nadolol, Nipradilol, Oxprenolol, Penbutolol, Pindolol, Propranolol, Talinolol, Tetraolol, Timolol and Toliprolol; Benzothiadiazine derivatives such as Althiazide, Bendroflumethiazide, Benzthiazide, Benzylhydrochlorothiazide, Buthiazide, Chlorothiazide, Chlorthalidone, Cyclopenthiazide, Cyclothiazide, Diazoxide, Epithiazide, Ethiazide, Fenquizone, Hydrochlorothiazide, Hydroflumethiazide, Methyclothiazide, Meticrane, Metolazone, Paraflutizide, Polythiazide, Tetrachlormethiazide and Trichlormethiazide; N-Carboxyalkyl (petide/lactam) derivatives such as Alacepril, Captopril, Cilazapril, Delapril, Enalapril, Enalaprilat, Fosinopril, Lisinopril, Moveltipril, Perindopril, Quinapril and Ramipril; Dihydropyridine derivatives such as Amlodipine, Felodipine, Isradipine, Nicardipine, Nifedipine, Nilvadipine, Nisoldipine and Nitrendipine;

43. Guanidine derivatives such as Bethanidine, Debrisoquin, Guanabenz, Guanacline, Guanadrel, Guanazodine, Guanethidine, Guanfacine, Guanochlor, Guanoxabenz and Guanoxan; Hydrazines and phthalazines such as Budralazine, Cadralazine, Dihydralazine, Endralazine, Hydracarbazine, Hydralazine, Pheniprazine, Pildralazine and Todralazine; Imidazole derivatives such as Clonidine, Lofexidine, Phentolamine, Tiamenidine and Tolonidine; Quaternary ammonium compounds Azamethonium Bromide, Chlorisondamine Chloride, Hexamethonium, Pentacynium Bis (methyl sulfate), Pentamethonium Bromide, Pentolinium Tartate, Phenactopinium Chloride and Trimethidiunum-Methosulfate; Quinazoline derivatives such as Alfuzosin, Bunazosin, Doxazosin, Prasosin, Terazosin and Trimazosin; Reserpine derivatives such as Bietaserpine, Deserpidine, Rescinnamine, Reserpine and Syrosingopine; Sulfonamide derivatives such as Ambuside, Clopamide, Furosemide, Indapamide, Quinethazone, Tripamide and Xipamide; and others such as Ajmaline, γ-AminobutYric Acid, Bufeniode, Chlorthalidone, Cicletaine, Ciclosidomine, Cryptenamine Tannates, Fenoldopam, Flosequinan, Indoramin, Ketanserin, Metbutamate, Mecamylamine, Methyldopa, Methyl 4-Pyridyl Ketone Thiosemicarbarzone, Metolazone, Minoxidil, Muzolimine, Pargyline, Pempidine, Pinacidil, Piperoxan, Primaperone, Protoveratrines, Raubasine, Rescimetol, Rilmenidene, Saralasin, Sodium Nitroprusside, Ticrynafen, Trimethaphan Camsylate, Tyrosinase and Urapidil.

44. Antihyperthyroids such as 2-Amino-4-methylthiazole, 2-Aminothiazole, Carbimazole, 3,5-Dibromo-L-tyrosine, 3,5-Diiodotyrosine, Hinderin, Iodine, Iothiouracil, Methimazole, Methylthiouracil, propylthiouracil, Sodium Perchlorate, Thibenzazoline, Thiobarbital and 2-Thiouracil.

45. Antihypotensive drugs such as Amezinium Methyl Sulfate, Angiotensin Amide, Dimetofrine, Dopamine, Etifelmin, Etilefrin, Gepefrine, Metaraminol, Midodrine, Norepinephrine, Pholedrinead and Synephrine.

46. Antihypothyroid drugs such as Levothyroxine Sodium, Liothyronine, Thyroid, Thyroidin, Thyroxine, Tiatricol and TSH.

47. Anti-Inflammatory (non-steroidal) drugs, including: Aminoarylcarboxylic acid derivatives such as Enfenamic Acid, Etofenamate, Flufenamic Acid, Isonixin, Meclofenamic Acid, Mefanamic Acid, Niflumic Acid, Talniflumate, Terofenamate and Tolfenamic Acid; Arylacetic acid derivatives such as Acemetacin, Alclofenac, Amfenac, Bufexamac, Cinmetacin, Clopirac, Diclofenac Sodium, Etodolac, Felbinac, Fenclofenac, Fenclorac, Fenclozic Acid, Fentiazac, Glucametacin, Ibufenac, Indomethacin, Isofezolac, Isoxepac, Lonazolac, Metiazinic Acid, Oxametacine, Proglumetacin, Sulindac, Tiaramide, Tolmetin and Zomepirac; Arylbutyric acid derivatives such as Bumadizon, Butibufen, Fenbufen and Xenbucin; Arylcarboxylic acids such as Clidanac, Ketorolac and Tinoridine; Arylpropionic acid derivatives such as Alminoprofen, Benoxaprofen, Bucloxic Acid, Carprofen, Fenoprofen, Flunoxaprofen, Flurbiprofen, Ibuprofen, Ibuproxam, Indoprofen, Ketoprofen, Loxoprofen, Miroprofen, Naproxen, Oxaprozin, Piketoprofen, Pirprofen, Pranoprofen, Protizinic Acid, Suprofen and Tiaprofenic Acid; Pyrazoles such as Difenamizole and Epirizole; Pyrazolones such as Apazone, Benzpiperylon, Feprazone, Mofebutazone, Morazone, Oxyphenbutazone, Phenybutazone, Pipebuzone, Propyphenazone, Ramifenazone, Suxibuzone and Thiazolinobutazone; Salicylic acid derivatives such as Acetaminosalol, Aspirin, Benorylate, Bromosaligenin, Calcium Acetylsalicylate, Diflunisal, Etersalate, Fendosal, Gentisic Acid, Glycol Salicylate, Imidazole Salicylate, Lysine Acetylsalicylate, Mesalamine, Morpholine Salicylate, 1-Naphthyl Salicylate, Olsalazine, Parsalmide, Phenyl Acetylsalicylate, Phenyl Salicylate, Salacetamide, Salicylamine O-Acetic Acid, Salicylsulfuric Acid, Salsalate and Sulfasalazine; Thiazinecarboxamides such as Droxicam, Isoxicam, Piroxicam and Tenoxicam; and others such as .epsilon.-Acetamidocaproic Acid, S-Adenosylmethionine, 3-Amino-4-hydroxybutyric Acid, Amixetrine, Bendazac, Benzydamine, Bucolome, Difenpiramide, Ditazol, Emorfazone, Guaiazulene, Nabumetone, Nimesulide, Orgotein, Oxaceprol, Paranyline, Perisoxal, Pifoxime, Proquazone, Proxazole and Tenidap.

48. Antimalarial drugs such as Acedapsone, Amodiaquin, Arteether, Artemether, Artemisinin, Artesunate, Bebeerine, Berberine, Chirata, Chlorguanide, Chloroquine, Chlorproguanil, Cinchona, Cinchonidine, Cinchonine, Cycloguanil, Gentiopicrin, Halofantrine, Hydroxychloroquine, Mefloquine Hydrochloride, 3-Methylarsacetin, Pamaquine, Plasmocid, Primaquine, Pyrimethamine, Quinacrine, Quinine, Quinine Bisulfate, Quinine Carbonate, Quinine Dihydrobromide, Quinine Dihydrochloride, Quinine Ethylcarbonate, Quinine Formate, Quinine Gluconate, Quinine Hydriodide, Quinine Hydrochloride, Quinine Salicylate, Quinine Sulfate, Quinine Tannate, Quinine Urea Hydrochloride, Quinocide, Quinoline and Sodium Arsenate Diabasic.

49. Antimigraine drugs such as Alpiropride, Dihydroergotamine, Ergocomine, Ergocominine, Ergocryptine, Ergot, Ergotamine, Flumedroxone acetate, Fonazine, Lisuride, Methysergid(e), Oxetorone, Pizotyline and Sumatriptan.

50. Antinauseant drugs such as Acetylleucine Monoethanolamine, Alizapride, Benzquinamide, Bietanautine, Bromopride, Buclizine, Chlorpromazine, Clebopride, Cyclizine, Dimenhydrinate, Diphenidol, Domperidone, Granisetron, Meclizine, Methalltal, Metoclopramide, Metopimazine, Nabilone, Ondansteron, Oxypendyl, Pipamazine, Piprinhydrinate, Prochlorperazine, Scopolamine, Tetrahydrocannabinols, Thiethylperazine, Thioproperzaine and Trimethobenzamide.

51. Antineoplastic drugs, including: Alkylating agents, including: Alkyl sulfonates such as Busulfan, Improsulfan and Piposulfan; Aziridines such as Benzodepa, Carboquone, Meturedepa and Uredepa; Ethylenimines and methylmelamines such as Altretamine, Triethylenemelamine, Triethylenephosphoramide, Triethylenethiophosphoramide and Trimethylolomelamine; Nitrogen mustards such as Chlorambucil, Chlomaphazine, Chclophosphamide, Estramustine, Ifosfamide, Mechlorethamine, Mechlorethamine Oxide Hydrochloride, Melphalan, Novembichin, Phenesterine, Prednimustine, Trofosfamide and Uracil Mustard; Nitrosoureas such as Carmustine, Chlorozotocin, Foremustine, Lomustine, Nimustine and Ranimustine; and others such as Dacarbazine, Mannomustine, Mitobronitol, Mitolactol and Pipobroman; Antibiotics such as Aclacinomycins, Actinomycin $F_1$, Anthramycin, Azaserine, Bleomycins, Cactinomycin, Carubicin, Carzinophilin, Chromomycins, Dactinomycin, Daunorubicin, 6-Diazo-5-oxo-L-norleucine, Doxorubicin, Epirubicin, Mitomycins, Mycophenolic Acid, Nogalamycin, Olivomycins, Peplomycin, Plicamycin, Porfiromycin, Puromycin, Streptonigrin, Streptozocin, Tubercidin, Ubenimex, Zinostatin and Zorubicin; Antimetabolites, including: Folic acid analogs such as Denopterin, Methotrexate, Pteropterin and Trimetrexate; Purine analogs such as Fludarabine, 6-Mercaptopurine, Thiamiprine and Thioguanaine; and Pyrimidine analogs such as Ancitabine, Azacitidine, 6-Azauridine, Carmofur, Cytarabine, Doxifluridine, Enocitabine, Floxuridine, Fluroouracil and Tegafur; Enzymes such as L-Asparaginase; and others such as Aceglatone, Amsacrine, Bestrabucil, Bisantrene, Carboplatin, Cisplatin, Defofamide, Demecolcine, Diaziquone, Elfomithine, Elliptinium Acetate, Etoglucid, Etoposide, Gallium Nitrate, Hydroxyurea, Interferon-α, Interferon-β, Interferon-γ, Interleukine-2, Lentinan, Lonidamine, Mitoguazone, Mitoxantrone, Mopidamol, Nitracrine, Pentostatin, Phenarnet, Pirarubicin, Podophyllinicc Acid, 2-Ethythydrazide, Procarbazine, PSK®, Razoxane, Sizofiran, Spirogermanium, Taxol, Teniposide, Tenuazonic Acid, Triaziquone, 2,2',2"Trichlorotriethylamine, Urethan, Vinblastine, Vincristine and Vindesine;

52. Antineoplastic (hormonal) drugs, including: Androgens such as Calusterone, Dromostanolone Propionate, Epitiostanol, Mepitiostane and Testolactone; Antiadrenals such as Aminoglutethimide, Mitotane and Trilostane; Antiandrogens such as Flutamide and Nilutamide; and Antiestrogens such as Tamoxifen and Toremifene.

53. Antineoplastic adjuncts including folic acid replenishers such as Frolinic Acid.

54. Antiparkinsonian drugs such as Amantadine, Benserazide, Bietanautine, Biperiden, Bromocriptine, Budipine, Carbidopa, Deprenyl, Dexetimide, Diethazine, Droxidopa, Ethopropazine, Ethylbenzhydramine, Levodopa, Naxagolide, Pergolide, Piroheptine, Pridinol, Prodipine, Terguride, Tigloidine and Trihexyphenidyl Hydrochloride.

55. Antipheochromocytoma drugs such as Metyrosine, Phenoxybenzamine and Phentolamine.

56. Antipneumocystis drugs such as Effornithine, Pentamidine and Sulfamethoxazole.

57. Antiprostatic hypertrophy drugs such as Gestonorone Caproate, Mepartricin, Oxendolone and Finasteride (ProscarO).

58. Antiprotozoal drugs (Leshmania) such as Antimony Sodium Gluconate, Ethylstibamine, Hydroxystilbamidine, N-Methylglucamine, Pentamidine, Stilbamidine and Urea Stibamine.

59. Antiprotozoal drugs (Trichomonas) such as Acetarsone, Aminitrozole, Anisomycin, Azanidazole, Forminitrazole, Furazolidone, Hachimycin, Lauroguadine, Mepartricin, Metronidazole, Nifuratel, Nifuroxime, Nimorazole, Secnidazole, Silver Picrate, Tenonitrozole and Tinidazole.

60. Antiprotozoal drugs (Trypanosma) such as Benznidazole, Eflomithine, Melarsoprol, Nifurtimox, Oxophenarsine, Hydrochloride, Pentamidine, Propamidine, Puromycin, Quinapyramine, Stilbamidine, Suramin Sodium, Trypan Red and Tryparasmide.

61. Antipuritics such as Camphor, Cyproheptadine, Dichlorisone, Glycine, Halometasone, 3-Hydroxycamphor, Menthol, Mesulphen, Methdilazine, Phenol, Polidocanol, Risocaine, Spirit of Camphor, Thenaldine, Tolpropamine and Trimeprazine.

62. Antipsoriatic drugs such as Acitretin, Ammonium Salicylate, Anthralin, 6-Azauridine, Bergapten(e), Chrysarobin, Etretinate and Pyrogallol.

63. Antipsychotic drugs, including: Butyrophenones such as Benperidol, Bromperidol, Droperidol, Fluanisone, Haloperidol, Melperone, Moperone, Pipamperone, Sniperone, Timiperone and Trifluperidol; Phenothiazines such as Acetophenazine, Butaperazine, Carphenazine, Chlorproethazine, Chlorpromazine, Clospirazine, Cyamemazine, Dixyrazine, Fluphenazine, Imiclopazine, Mepazine, Mesoridazine, Methoxypromazine, Metofenazate, Oxaflumazine, Perazine, Pericyazine, Perimethazine, Perphenazine, Piperacetazine, Pipotiazine, Prochlorperazine, Promazine, Sulforidazine, Thiopropazate, Thioridazine, Trifluoperazine and Triflupromazine; Thioxanthenes such as Chlorprothixene, Clopenthixol, Flupentixol and Thiothixene; other tricyclics such as Benzquinamide, Carpipramine, Clocapramine, Clomacran, Clothiapine, Clozapine, Opipramol, Prothipendyl, Tetrabenazine, and Zotepine; and others such as Alizapride, Amisulpride, Buramate, Fluspirilene, Molindone, Penfluridol, Pimozide, Spirilene and Sulpiride.

64. Antipyretics such as Acetaminophen, Acetaminosalol, Acetanilide, Aconine, Aconite, Aconitine, Alclofenac, Aluminum Bis(acetylsalicylate), Aminochlorthenoxazin, Aminopyrine, Aspirin, Benorylate, Benzydamine, Berberine, p-Bromoacetanilide, Bufexamac, Bumadizon, Calcium Acetysalicylate, Chlorthenoxazin(e), Choline Salicylate, Clidanac, Dihydroxyaluminum Acetylsalicylate, Dipyrocetyl, Dipyrone, Epirizole, Etersalate, Imidazole Salicylate, Indomethacin, Isofezolac, p-Lactophenetide, Lysine Acetylsalicylate, Magnesium Acetylsalicylate, Meclofenamic Acid, Morazone, Morpholine Salicylate, Naproxen, Nifenazone, 5'-Nitro-2'propoxyacetanilide, propoxyacetanilide, Phenacetin, Phenicarbazide, Phenocoll, Phenopyrazone, Phenyl Acetylsalicylate, Phenyl Salicylate, Pipebuzone, Propacetamol, Propyphenazone, Ramifenazone, Salacetamide, Salicylamide 0-Acetic Acid, Sodium Salicylate, Sulfamipyrine, Tetrandrine and Tinoridine.

65. Antirickettsial drugs such as p-Aminobenzoic Acid, Chloramphenicol, Chloramphenicol Palmitate, Chloramphenicol Pantothenate and Tetracycline.

66. Antiseborrheic drugs such as Chloroxine, 3-O-Lauroylpyridoxol Diacetate, Piroctone, Pyrithione, Resorcinol, Selenium Sulfides and Tioxolone.

67. Antiseptics, including: Guanidines such as Alexidine, Ambazone, Chlorhexidine and Picloxydine; Halogens and halogen compounds such as Bismuth Iodide Oxide, Bismuth Iodosubgallate, Bismuth Tribromophenate, Bornyl Chloride, Calcium Iodate, Chlorinated Lime, Cloflucarban, Flurosalan, Iodic Acid, Iodine, Iodine Monochloride, Iodine Trichloride, Iodoform, Methenamine Tetraiodine, Oxychlorosene, Povidone-Iodine, Sodium Hypochlorite, Sodium Iodate, Symclosene, Thymol Iodide, Triclocarban, Triclosan and Troclosene Potassium; Mercurial compounds such as Hydragaphen, Meralein Sodium, Merbromin, Mercuric Chloride, Mercuric Chloride, Ammoniated, Mercuric Sodium p-Phenolsulfonate, Mercuric Succinimide, Mercuric Sulfide, Red, Mercurophen, Mercurous Acetate, Mercurous Chloride, Mercurous Iodide, Nitromersol, Potassium Tetraiodomercurate(II), Potassium Triiodomercurate(II) Solution, Thimerfonate Sodium and Thimerosal; Nitrofurans such as Furazolidone, 2-(Methoxymethyl)-5-nitrofuran, Nidroxyzone, Nifuroxime, Nifurzide and Nitrofurazone; Phenols such as Acetomeroctol, Bithionol, Cadmium Salicylate, Carvacrol, Chloroxylenol, Clorophene, Cresote, Cresol(s), p-Cresol, Fenticlom, Hexachlorophene, 1-Napthyl Salicylate, 2-Napthyl Salicylate, 2,4,6-Tribromo-m-cresol, and 3',4',5-Trichlorosalicylanilide; Quinolines such as Aminoquinuride, Benzoxiquine, Broxyquinoline, Chloroxine, Chlorquinaldol, Cloxyquin, Ethylhydrocupreine, Euprocin, Halquinol, Hydrastine, 8-Hydroxyquinoline, 8-Hydroxyquinoline Sulfate and Iodochlorhydroxyquin; and others such as Aluminum Acetate Solution, Aluminum Subacetate Solution, Aluminum Sulfate, 3-Amino-4-hydroxybutyric Acid, Boric Acid, Chlorhexidine, Chloroazodin, m-Cresyl Acetate, Cupric Sulfate, Dibromopropamidine, Ichthammol, Negatolg, Noxytiolin, Omidazole, β-Propiolactone, α-Terpineol.

68. Antispasmodic drugs such as Alibendol, Ambucetamide, Aminopromazine, Apoatropine, Bevonium Methyl Sulfate, Bietamiverine, Butaverine, Butropium Bromide, N-Butylscopolammonium Bromide, Caroverine, Cimetropium Bromide, Cinnamedrine, Clebopride, Coniine Hydrobromide, Coniine Hydrochloride, Cyclonium Iodide, Difemerine, Diisopromine, Dioxaphetyl Butyrate, Diponium Bromide, Drofenine, Emepronium Bromide, Ethaverine, Feclemine, Fenalamide, Fenoverine, Fenpiprane, Fenpiverinium Bromide, Fentonium Bromide, Flavoxate, Flopropione, Gluconic Acid, Guaiactamine, Hydramitrazine, Hymecromone, Leiopyrrole, Mebeverine, Moxaverine, Nafiverine, Octamylamine, Octaverine, Pentapiperide, Phenamacide Hydrochloride, Phloroglucinol, Pinaverium Bromide, Piperilate, PipoxolanHydrochloride, Pramiverin, Prifinium Bromide, Properidine, Propivane, Propyromazine, Prozapine, Racefemine, Rociverine, Spasmolytol, Stilonium Iodide, Sultroponium, Tiemonium Iodide, Tiquizium Bromide, Tiropramide, Trepibutone, Tricromyl, Trifolium, Trimebutine, N,N-1Trimethyl-3,3-diphenyl-propylamine, Tropenzile, Trospium Chloride and Xenytropium Bromide.

69. Antithrombotic drugs such as Anagrelide, Argatroban, Cilostazol, Daltroban, Defibrotide, Enoxaparin, Fraxiparine®, Indobufen, Lamoparan, Ozagrel, Picotamide, Plafibride, Tedelparin, Ticlopidine and Triflusal.

70. Antitussive drugs such as Allocamide, Amicibone, Benproperine, Benzonatate, Bibenzonium Bromide, Bromoform, Butamirate, Butethamate, Caramiphen Ethanedisulfonate, Carbetapentane, Chlophedianol, Clobutinol, Cloperastine, Codeine, Codeine Methyl Bromide, Codeine N-Oxide, Codeine Phosphate, Codeine Sulfate, Cyclexanone, Dextromethorphan, Dibunate Sodium, Dihydrocodeine, Dihydrocodeinone Enol Acetate, Dimemorfan, Dimethoxanate, α,α-Diphenyl-2-piperidinepropanol, Dropropizine, Drotebanol, Eprazinone, Ethyl Dibunate, Ethylmorphine, Fominoben, Guiaiapate, Hydrocodone, Isoaminile, Levopropoxyphene, Morclofone, Narceine, Normethadone, Noscapine, Oxeladin, Oxolamine, Pholcodine, Picoperine, Pipazethate, Piperidione, Prenoxdiazine Hydrochloride, Racemethorphan, Taziprinone Hydrochloride, Tipepidine and Zipeprol.

71. Antiulcerative drugs such as Aceglutamide Aluminum Complex, .epsilon.-Acetamidocaproic Acid Zinc Salt, Acetoxolone, Arbaprostil, BenexateHydrochloride, Bismuth Subcitrate Sol (Dried), Carbenoxolone, Cetraxate, Cimetidine, Enprostil, Esaprazole, Famotidine, Ftaxilide, Gefarnate, Guaiazulene, Irsogladine, Misoprostol, Nizatidine, Omeprazole, Ornoprostil, γ-Oryzanol, Pifarnine, Pirenzepine, Plaunotol, Ranitidine, Rioprostil, Rosaprostol, Rotraxate, Roxatidine Acetate, Sofaicone, Spizofurone, Sucralfate, Teprenone, Trimoprostil, Thrithiozine, Troxipide and Zolimidine.

72. Antiurolithic drugs such as Acetohydroxamic Acid, Allopurinol, Potassium Citrate and Succinimide.

73. Antiviral drugs, including: Purines and pyrimidinones such as Acyclovir, Cytarabine, Dideoxyadenosine, Dideoxycytidine, Dideoxyinosine, Edoxudine, Floxuridine, Ganciclovir, Idoxuridine, Inosine Pranobex, MADU, Trifluridine, Vidrarbine and Zidovudiine; and others such as Acetylleucine Monoethanolamine, Amantadine, Amidinomycin, Cuminaldehyde Thiosemicarbzone, Foscarnet Sodium, Interferon-α, Interferon-β, Interferon-γ, Kethoxal, Lysozyme, Methisazone, Moroxydine, Podophyllotoxin, Ribavirin, Rimantadine, Stallimycin, Statolon, Tromantadine and Xenazoic Acid.

74. Anxiolytic drugs, including: Arylpiperaz ines such as Buspirone, Gepirone and Ipsapirone; Benzodiazepine derivatives such as Alprazolam, Bromazepaam, Camazepam, Chlordiazepoxide, Clobazam, Clorazepate, Chotiazepam, Cloxazolam, Diazepam, Ethyl Loflazepate, Etizolam, Fluidazepam, Flutazolam, Flutoprazepam, Halazepam, Ketazolam, Lorazepam, Loxapine, Medazepam, Metaclazepam, Mexazolam, Nordazepam, Oxazepam, Oxazolam, Pinazepam, Prazepam and Tofisopam; Carbamates such as Cyclarbamate, Emylcamate, Hydroxyphenamate, Meprobamate, Phenprobamate and Tybamate; and others such as Alpidem, Benzoctamine, Captodiamine, Chlormezanone, Etifoxine, Fluoresone, Glutamic Acid, Hydroxyzine, Mecloralurea, Mephenoxalone, Oxanamide, Phenaglycodol, Suriclone.

75. Benzodiazepine antagonists such as Flumazenil.

76. Bronchodilators, including: Ephedrine derivatives such as Albuterol, Bambuterol, Bitolterol, Carbuterol, Clenbuterol, Clorprenaline, Dioxethedrine, Ephedrine, Epiniphrine, Eprozinol, Etafedrine, Ethylnorepinephrine, Fenoterol, Hexoprenaline, Isoetharine, Isoproterenol, Mabuterol, Metaproterenol, N-Methylephedrine, Pirbuterol, Procaterol, Protokylol, Reproterol, Rimiterol, Soterenol, Terbutaline and Tulobuterol; Quaternary ammonium compounds such as Bevonium Methyl Sulfate, Clutropium Bromide, Ipratropium Bromide and Oxitropium Bromide; Xanthine derivatives such as Acefylline, Acefylline Piperazine, Ambuphylline, Aminophylline, Bamifylline, choline Theophyllinate, Doxofylline, Dyphylline, Enprofylline, Etamiphyllin, Etofylline, Guaithylline, Proxyphylline, Theobromine, 1-Theobromineacetic Acid and Theophylline; and others such as Fenspiride, Medibazine, Methoxyphenanime and Tretoquinol.

77. Calcium channel blockers, including: Arylalkylamines such as Bepridil, Ditiazem, Fendiline, Gallopanil, Prenylamine, Terodiline and Verapamil; Dihydropyridine derivatives such as Felodipine, Isradipine, Nicardipine, Nifedipine, Nilvadipine, Nimodipine, Nisoldipine and Nitrendipine; Piperazine derivatives such as Cinnarizine, Flunarisine and Lidoflazine; and others such as Bencyclane, Etafenone and Perhexiline.

78. Calcium regulators such as Calcifediol, Calcitonin, Calcitriol, Clodronic Acid, Dihydrotachysterol, Elcatonin, Etidronic Acid, Ipriflavone, Pamidronic Acid, Parathyroid Hormone and Teriparatide Acetate.

79. Cardiotonics such as Acefylline, Acetyldigititoxins, 2-Amino-4-picoline, Amrinone, Benfurodil Hemisuccinate, Buclasdesine, Cerberoside, Camphotamide, Convallatoxin, Cymarin, Denopamine, Deslanoside, Ditalin, Digitalis, Digitoxin, Digoxin, Dobutamine, Dopamine, Dopexamine, Enoximone, Erythrophleine, Fenalcomine, Gitalin, Gitoxin, Glycocyamine, Heptaminol, Hydrastinine, Ibopamine, Lanotodises, Metamivam, Milrinone, Neriifolin, Oleandrin, Ouabain, Oxyfedrine, Prenalterol, Proscillaridin, Resibufogenin, Scillaren, Scillarenin, Strophanthin, Sulmazole, Theobromine and Xamoterol.

80. Chelating agents such as Deferozmine, Ditiocarb Sodium, Edetate Calcium Disodium, Edetate Disodium, Edeate Sodium, Edetate Trisodium, Penicillamine, Pentetate Calcium Trisodium, Pentectic Acid, Succimer and Trientine.

81. Cholecystokinin antagonists such as Proglumide.

82. Cholelitholytic agents such as Chenodiol, Methyl tert-Butyl Ether, Monooctanoin and Ursodiol 83. Choleretics such as Alibendol, Anethole Trithion, Azintamide, Cholic Acid, Cicrotoic Acid, Clanobutin, Cyclobutyrol, Cyclovalone, Cynarin(e), Dehydrocholic Acid, Deoxycholic Acid, Dimecrotic Acid, α-Ethylbenzyl Alcohol, Exiproben, Feguprol, Fencibutirol, Fenipentol, Florantyrone, Hymecromone, Menbutone, 3-(o-Methoxyphenyl)-2-phenylacrylic Acid, Metochalcone, Moquizone, Osalmid, Ox Bile Extract, 4.4'-Oxydi-2-butanol, Piprozolin, Prozapine, 4-Salicyloylmorpholine, Sincalide, Taurocholic Acid, Timonacic, Tocamphyl, Trepibutone and Vanitiolide.

84. Cholinergic agents such as Aceclidine, Acetylcholine Bromide, Acetylcholide Chloride, Aclatonium Napadisilate, Benzpyrinium Bromide, Bethanechol chloride, Carbachol, Carpronium chloride, Demecarium Bromide, Dexpanthenol, Diisopropyl Paraoxon, Echothiophate Iodide, Edrophomium chloride, Eseridine, Furtrethonium, Isoflurophate, Methacholine chloride, Muscarine, Neostigmine, Oxapropanium Iodide, Physostigmine and Pyridostigmine Bromide.

85. Cholinesterase inhibitors such as Ambenonium Chloride, Distigmine Bromide and Galanthamine.

86. Cholinesterase reactivators such as Obidoximine Chloride and Pralidoxime Chloride.

87. Central nervous system stimulants and agents such as Amineptine, Amphetimine, Amphetaminil, Bemegride, Benzphetamine, Brucine, Caffeine, Chlorphentermine, Clofenciclan, Clortermine, Coca, Demanyl Phosphate, Dexoxadrol, Dextroamphetamine Sulfate, Diethlpropion, N-Ethytlamphetamine, Ethamivan, Etifelmin, Etryptamine, Fencamfamine, Fenethylline, Fenosolone, Flurothyl, Hexacyclonate Sodium, Homocamfin, Mazindol, Megexamide, Methamphetamine, Methylphenidate, Nikethamide, Pemoline, Pentylenetetrazole, Phenidimetrazine, Phenmetrazine, Phentermine, Picrotoxin, Pipradrol, Prolintane and Pyrovalerone.

88. Decongestants such as Amidephrine, Cafaminol, Cyclopentamine, Ephedrine, Epinephrine, Fenoxazoline, Indanazoline, Metizoline, Naphazoline, Nordefrin Hydrochloride, Octodrine, Oxymetazoline, Phenylephrine Hydrochloride, Phenylpropanolamine Hydrochloride, Phenylpropylmethylamine, Propylhexedrine, Pseudoephedrine, Tetrahydrozoline, Tymazoline and Xylometazoline.

89. Dental carries prophylactics such as Sodium Fluoride.

90. Depigmentors such as Hydroquinine, Hydroquinone and Monobenzone.

92. Diuretics, including: Organomercurials such as Chlormerodrin, Meralluride, Mercamphamide, Mercaptomerin Sodium, Mercumallylic Acid, Mercumatilin Sodium, Mercurous Chloride and Mersalyl; Pteridines such as Furterene and Triamterene; Purines such as Acefylline, 7-Morpholinomethyltheophylline, Pamabrom, Protheobromine and Theobromine; Steroids such as Canrenone, Oleandrin and Spironolactone; Sulfonamide derivatives such as Acetazolmide, Ambuside, Azosemide, Bumetanide, Butazolamide, Chloraminophenamide, Clofenamide, Clopamide, Clorexolene, Diphenylmethane-4.4'-disulfonamide, Disulfamide, Ethoxzolamide, Furosemide, Indapamide, Mefruside, Methazolamide, Piretanide, Quinethazone, Torasemide, Tripamide and Xipamide; Uracils such as Aminometradine and Amisometradine; others such as Amanozine, Amiloride, Arbutin, Chlorazanil, Ethacrynic Acid, Etozolin, Hydracarbazine, Isosorbide, Mannitol, Metochalcone, Muzolimine, Perhexiline, Ticrynafen and Urea.

92. Dopamine receptor agonists such as Bromocriptine, Dopexamine, Fenoldopam, Ibopamine, Lisuride, Naxagolide and Pergolide.

93. Ectoparasiticides such as Amitraz, Benzyl Benzoate, Carbaryl, Crotamiton, DDT, Dixanthogen, isobomyl Thiocyanoacetate-Technical, Lime Sulfurated Solution, LIndane, Malathion, Mercuric Oleate, Mesulphen and Sulphur—Pharmaceutical; and Mucolytic enzymes such as Lysozyme.

94. Enzyme inducers (hepatic) such as Flumecinol.

95. Estrogens, including: Nonsteroidal estrogens such as Benzestrol, Broparoestrol, Chlorotrianisene, Dienestrol, Diethylstilbestrol, Diethylstilbestrol Diproprionate, Dimestrol, Fosfestrol, Hexestrol, Methallenestril and Methestrol; and Steroidal estrogens such as Colpormon, Conjugated Estrogenic Hormones, Equilenin, Equilin, Estradiol, Estradiol Benzoate, Estradiol 17β-Cypionate, Estriol, Estrone, Ethinyl Estradiol, Mestranol, Moxestrol, Mytatrienediol, Quinestradiol and Quinestrol.

96. Gastric secretion inhibitors such as Enterogastrone and Octreotide.

97. Glucocorticoids such as 21-Acetoxyprefnenolone, Aalclometasone, Algestone, Amicinonide, Beclomethasone, Betamethasone, Budesonide, Chloroprednisone, Clobetasol, Blovetasone, Clocortolone, Cloprednol, Corticosterone, Cortisone, Cortivazol, Deflazacort, Desonide, Desoximetasone, Dexamethasone, Diflorasone, Diflucortolone, Difluprednate, Enoxolone, Fluazacort, Flucloronide, Flumehtasone, Flunisolide, Fluocinolone Acetonide, Fluocinonide, Fluocortin Butyl, Fluocortolone, Fluorometholone, Fluperolone Acetate, Fluprednidene Acetate, Fluprednisolone, Flurandrenolide, Formocortal, Halcinonide, Halometasone, Halopredone Acetate, Hydrocortamate, Hydrocortisone, Hydrocortisone Acetate, ydrocortisone Phosphate, Hydrocortisone 21-Sodium Succinate, Hydrocortisone Tebutate, Mazipredone, Medrysone, Meprednisone, Methyolprednisolone, Mometasone Furoate, Paramethasone, Prednicarbate, Prednisolone, Prednisolone 21-Diethylaminoacetate, Prednisone Sodium Phosphate, Prednisolone Sodium Succinate, Prednisolone Sodium 21-m-Sulfobenzoate, Prednisolone 21-Stearoylglycolate, Prednisolone Tebutate, Prednisolone 21-Trimethylacetate, Prednisone, Prednival, Prednylidene, Prednylidene 21-Diethylaminoacetate, Tixocortal, Triamcinolone, Triamcinolone Acetonide, Triamcinolone Benetonide and Triamcinolone Hexacetonide.

98. Gonad-Stimulating principles such as Buserelin, Clomiphene, Cyclofenil, Epimestrol, FSH, HCG and LH-RH.

99. Gonadotropic hormones such as LH and PMSG.

100. Growth hormone inhibitors such as Octreotide and Somatostatin.

101. Growth hormone releasing factors such as Semorelin.

102. Growth stimulants such as Somatotropin.

103. Hemolytic agents such as Phenylhydrazine and Phenylhydraz ine Hydrochloride.

104. Heparin antagonists such as Hexadimethrine Bromide and Protamines.

105. Hepatoprotectants such as S-Adenosylmethionine, Betaine, Catechin, Citolone, Malotilate, Orazamide, Phosphorylcholine, Protoporphyrin IX, Silymarin-Group, Thiotic Acid and Tiopronin.

106. Immunomodulators such as Amiprilose, Bucillamine, Ditiocarb Sodium, Inosine Pranobex, Interferon-y, Interleukin-2, Lentinan, Muroctasin, Platonin, Procodazole, Tetramisole, Thymomodulin, Thymopentin and Ubenimex.

107. Immunosuppressants such as Azathioprine, Cyclosporins and Mizoribine.

108. Ion exchange resins such as Carbacrylic Resins, Cholestyramine Resin, Colestipol, Polidexide, Resodec and Sodium Polystyrene Sulfonate.

109. Lactation stimulating hormone such as Prolactin.

110. LH-RH agonists such as Buserelin, Goserelin, Leuprolide, Nafarelin, and Triptorelin.

111. Lipotropic agents such as N-Acetylmethionine, Choline Chloride, Choline Dehydrocholate, Choline Dihydrogen Citrate, Inositol, Lecithin and Methionine.

112. Lupus erythematosus suppressants such as Bismuth Sodium Triglycollamate, Bismuth Subsalicylate, Chloroquine and Hydroxychloroquine.

113. Mineralcorticoids such as Aldosterone, Deoxycorticosterone, Deoxycorticosterone Acetate and Fludrocortisone.

114. Miotic drugs such as Carbachol, Physostigmine, Pilocarpine and Pilocarpus.

115: Monoamine oxidase inhibitors such as Deprenyl, Iproclozide, Iproniazid, Isocarboxazid, Moclobemide, Octomoxin, Pargyline, Phenelzine, Phenoxypropazine, Pivalylbenzhydrazine, Prodipine, Toloxatone and Tranylcypromine.

116. Mucolytic agents such as Acetylcysteine, Bromhexine, Carbocysteine, Domiodol, Letosteine, Lysozyme, Mecysteine Hydrochloride, Mesna, Sobrerol, Stepronin, Tiopronin and Tyloxapol.

117. Muscle relaxants (skeletal) such as Afloqualone, Alcuronium, Atracurium Besylate, Baclofen, Benzoctamine, Benzoquinonium Chloride, C-Calebassine, Carisoprodol, Chlormezanone, Chlorphenesin Carbamate, Chlorproethazine, Chlozoxaz one, Curare, Cyclarbamate, Cyclobenzaprine, Dantrolene, Decamethonium Bromide, Diazepam, Eperisone, Fazadinium Bromide, Flumetramide, Gallamine Triethiodide, Hexacarbacholine Bromide, Hexafluorenium Bromide, Idrocilamide, Lauexium Methyl Sulfate, Leptodactyline, Memantine, Mephenes in, Mephenoxalone, Metaxalone, Methocarbamol, Metocurine Iodide, Nimetazepam, Orphenadrine, Pancuronium Bromide, Phenprobamate, Phenyramidol, Pipecurium Bromide, Promoxolane, Quinine Sulfate, Styramate, Succinylcholine Bromide, Succinylcholine Chloride, Succinylcholine Iodine, Suxethonium Bromide, Tetrazepam, Thiocolchicoside, Tizanidine, Tolperisone, Tubocurarine Chloride, Vecuronium Bromide and Zoxolamine.

118: Narcotic antagonists such as Amiphenazole, Cyclazocine, Levallorphan, Nadide, Nalmfene, Nalorphine, Nalorphine Dinicotinate, Naloxone and Naltrexone.

119. Neuroprotective agents such as Dizocilpine.

120. Nootropic agents such as Aceglutamide, Acetylcarnitine, Aniracetam, Bifematlane, Exifone, Fipexide, Idebenone, Indeloxazune Hydrochloride, Nizofenone, Oxiracetam, Piracetam, Propentofylline, Pyritinol and Tacrine.

121. Ophthalmic agents such as 15-ketoprostaglandins.

122. Ovarian hormone such as relaxin.

123. Oxytocic drugs such as Carboprost, Cargutocin, Deaminooxytocin, Ergonovine, Gemeprost, Methylergonovine, Oxytocin, Pituitary (Posterior), Prostaglandin E2, Prostaglandin F2α and Sparteine.

124. Pepsin inhibitors such as Sodium Amylosulfate.

125. Peristaltic stimulants such as Cisapride.

126. Progestogens such as Allylestrenol, Anagestone, Chlormadinone Acetate, Delmadinone Acetate, Demegestone, Desogestrel, Dimethisterone, Dydrogesterone, Ethisterone, Ethynodiol, Flurogestone Acetate, Gestodene, Gestonorone Caproate, Haloprogesterone, 17-Hydroxy-16-methylene-progesterone, 17α-Hydroxyprogesterone, 17α-Hydroxygesterone Caproate, Lynestrenol, Medrogestone, Medroxyprogesterone, Megestrol Acetate, Melengestrol, Norethindrone, Norethynodrel, Norgesterone, Norgestimate, Norgestrel, Norgestrienone, Norvinisterone, Pentagestrone, Progesterone, Promegestone, Quingestrone and Trengestone.

127. Prolactin inhibitors such as Metergoline.

128. Prostaglandins and prostaglandin analogs such as Arbaprostil, Carboprost, Enprostil, Bemeprost, Limaprost, Misoprostol, Omoprostil, Prostacyclin, Prostaglandin E1, Prostaglandin E2, Prostagland in F2α, Rioprostil, Rosaprostol, Sulprostone and Trimoprostil.

129. Protease inhibitors such as Aprotinin, Camostat, Gabexate and Nafamostat.

130. Respiratory stimulants such as Almitrine, Bemegride, Carbon Dioxide, Cropropamide, Crotethamide, Dimefline, Dimorpholamine, Doxapram, Ethamivan, Fominoben, Lobeline, Mepixanox, Metamivam, Nikethamide, Picrotoxin, Pimeclone, Pyridofylline, Sodium Succinate and Tacrine.

131. Sclerosing agents such as Ethanolamine, Ethylamine, 2-Hexyldecanoic Acid, Polidocanol, Quinine Bisulfate, Quinine Urea Hydrochloride, Sodium Ricinoleate, Sodium Tetradecyl Sulfate and Tribenoside.

132. Sedatives and hypnotics, including: Acyclic ureides such as Acecarbromal, Apronalide, Bomisovalum, Capuride, Carbromal and Ectylurea; Alcohols such as Chlorhexadol, Ethchlorvynol, Meparfynol, 4-Methyl-5-thiazoleethanol, tert-Pentyl Alcohol and 2,2,2-Trichloroethanol; Amides such as Butoctamide, Diethylbromoacetamide, Ibrotamide, Isovaleryl Diethylamide, Niaprazine, Tricetamide, Trimetozine, Zolpidem and Zopiclone; Barbituric acid derivatives such as Allobarbital, Amobarbital, Aprobarbital, Barbital, Brallabarbital, Butabarbital Sodium, Butalbital, Butallylonal, Butethal, Carbubarb, Cyclobarbital, Cyclopentobarbital, Enallylpropymal, 5-Ethyl-5-(1-piperidyl) barbituric Acid, 5-Furfuryl-5-isopropylbarbituric Acid, Heptabarbital, Hexethal Sodium, Hexobarbital, Mephobarbital, Methitural, Narcobarbital, Nealbarbital, Pentobarbital Sodium, Phenallymal, Phenobarbital, Phenobarbital Sodium, Phenylmethylbarbituric Acid, Probarbital, Propallylonal, Proxibarbal, Reposal, Secobarbital Sodium, Talbutal, Tetarbarbital, Vinbarbital Sodium and Vinylbital; Benzodiazepine derivatives such as Brotizolam, Doxefazepam, Estazolam, Flunitrazepam, Flurazepam, Haloxazolam, Loprazolam, Lormetazepam, Nitrazepam, Quazepam, Temasepam and Triazolam; Bromides such as Ammonium Bromide, Calcium Bromide, Calcium Bromolactobionate, Lithium Bromide, Magnesium Bromide, Potassium Bromide and Sodium Bromide; Carbamates such as Amyl Carbamate-Tertiary, Ethinamate, Hexaprpymate, Meparfynol Carbamate, Novonal and Trichlorourethan; Chloral derivatives such as Carbocloral, Chloral Betaine, Chloral Formamide, Chloral Hydrate, Chloralantipyrine, Dichloralphenazone, Pentaerythritol Chloral and Triclofos; Piperidinediones such as Glutehimide, Methyprylon, Piperidione, Pyrithyldione, Taglutimide and Thalidomide; Quinazolone derivatives such as Etaqualone, Mecloqualone and Methaqualone; and others such as Acetal, Acetophenone, Aldol, Ammonium Valerate, Amphenidone, d-Bornyl α-Bromoisovalerate, d-Bornyl Isovalerate, Bromoform, Calcium 2-Ethylbutanoate, Carfinate, α-Chlorolose, Clomethiazole, Cypripedium, Doxylamine, Etodroxizine, Etomidate, Fenadiazole, Homofenazine, Hydrobromic Acid, Mecloxamine, Menthyl Valerate, Opium, Paraldehyde, Perlapine, Propiomazine, Rilmazafone, Sodium Oxybate, Sulfonethylmethane and Sulfonmethane.

133. Thrombolytic agents such as APSAC, Plasmin, Pro-Urokinase, Streptokinase, Tissue Plasminogen Activator and Urokinase.

134. Thyrotropic hormones such as TRH and TSH.

135. Uricosurics such as Benzbromarone, Ethebenecid, Orotic Acid, Oxycinchophen, Probenecid, Sulfinpyrazone, Ticrynafen and Zoxazolamine.

136. Vasodilators (cerebral) such as Bencyclane, Cinnarizine, Citicoline, Cyclandelate, Ciclonicate, Diisopropylamine Dichloractetate, Ebumrnamonine, Fenoxedil, Flunarizine, Ibudilast, Ifenprodil, Nafronyl, Nicametate, Nicergoline, Nimodipine, Papaverine, Pentifylline, Tinofedrine, Vincamine, Vinpocetine and Viquidil.

137. Vasodilators (coronary) such as Amotriphene, Bendazol, Benfurodil Hemisuccinate, Benziodarone, Chloacizine, Chromonar, Clobenfurol, Clonitrate, Dilazep, Dipyridamole, Droprenilamine, Efloxate, Erythritol, Erythrityl Tetranitrate, Etafenone, Fendiline, Floredil, Ganglefene, Hexestrol Bis(β-diethylaminoethyl ether), Hexobendine, Itramin Tosylate, Khellin, Lidoflazine, Mannitol Hexanitrate, Medibazine, Nicorandil, Nitroglycerin, Pentaerythritol Tetranitrate, Pentrinitrol, Perhexiline, Pimefylline, Prenylamine, Propatyl Nitrate, Pyridofylline, Trapidil, Tricromyl, Trimetazidine, Trolnitrate Phosphate and Visnadine.

138. Vasodilators (peripheral) such as Aluminum Nicotinate, Bamethan, Bencyclane, Betahistine, Bradykinin, Brovincamine, Bufoniode, Buflomedil, Butalamine, Cetiedil, Ciclonicate, Cinepazide, Cinnarizine, Cyclandelate, Diisopropylamine Dichloracetate, Eledoisin, Fenoxidil, Flunarisine, Heronicate, Ifenprodil, Inositol Niacinate, Isoxsuprine, Kallidin, Kallikrein, Moxisylyte, Nafronyl, Nicametate, Nicergoline, Nicofuranose, Nicotinyl Alcohol, Nylidrin, Pentifylline, Pentoxifylline, Piribedil, Protaglandin $E_1$, Suloctidil and Xanthinal Niacinate.

139. Vasoprotectants such as Benzarone, Bioflavonoids, Chromocarb, Clobeoside, Diosmin, Dobesilate Calcium, Escin, Rolescutol, Leucocyanidin, Metescufylline, Quercetin, Rutin and Troxerutin.

140. Vitamins, vitamin sources, and vitamin extracts such as Vitamins A, B, C, D, E, and K and derivatives thereof, Calciferols, Glycyrrhiza and Mecobalamin.

141. Vulnerary agents such as Acetylcysteine, Allantoin, Asiaticoside, Cadexomer Iodine, Chitin, Dextranomer and Oxaceprol.

The initial crystallization phase of the process requires use of a solvent and anti-solvent, wherein the solvent and anti-solvent system consists of one or more pharmaceutically acceptable solvents (here defined as Class 3 solvents as designated in the European Pharmacopea, 2002, 4th edition or appear as monographs in European Pharmacopea or in the United States Pharmacopea).

Examples of solvents and anti-solvents include aprotic solvents (DMSO, N-methylpyrrolidone, and ethers), alcohols (ethanol, methanol, benzyl alcohol and isopropanol), hydrocarbons (hexane, cyclo-hexane and heptane), and other protic solvents (water and acetic acid). Examples of solvent (e.g., common solvents and anti-solvents) for use in the inventive compositions and methods of the invention include, but are not limited to, transesterfied vegetable oils, 1-pentanol, 1-propanol, 1-butanol, 2-butanol, 2-methyl-1-propanol, 2-piperidone, 2-pyrrolidone, 3-methyl-1-butanol, acetone, acetyl tributyl citrate, acetyl triethylcitrate, acetylated glycerol fatty acid esters, acetylated monoglycerides and sterols, benzyl alcohol, butanediol and isomers thereof, butanol, butyl acetate, $C_{10}$ fatty acids, $C_8$ and $C_{10}$ mono and diglycerides and mixtures thereof, $C_8$ and $C_{10}$ triglycerides, cumene, dimethyl isosorbide, dimethyl sulphoxide, ethanol, ethyl acetate, ethyl butyrate, ethyl caprylate, ethyl ether, ethyl formate, ethyl oleate, ethyl propionate, fatty acids, glycerol, glycerol fatty acid esters, glyceryl dicaprate, glyceryl dicaprylate, glyceryl dilaurate, glyceryl dioleate, glyceryl monocaprate, glyceryl monocaprylate, glyceryl monolaurate, glyceryl monooleate, glycofurol, heptane, hydrogenated vegetable oils, isobutyl acetate, isopropanol, isopropyl acetate, lactic acid conjugates of mono- and diglycerides, lauric acid, lower alcohol fatty acid esters, methoxy PEG, methyl acetate, methylethylketone, methylisobutylketone, N-hydroxyalkylpyrrolidone, N-methylpyrrolidone, oleic acid, PEG 2-4 oleate, PEG 3-16 castor oil, PEG 5-10 hydrogenated castor oil, PEG 6-20 almond oil, PEG 6-20 corn oil, PEG-20 almond oil, PEG-20 corn oil, PEG-4 dilaurate, PEG-4 dioleate, PEG-4 distearate, PEG-6 corn oil, PEG-6 dioleate, PEG-6 distearate, PEG-6 olive oil, PEG-6 palm kernel oil, PEG-6 peanut oil, PEG-8 dioleate, pentaerythritol, pentane, polyethylene glycol, polyethylene glycol 200-600, polyethylene glycol glycerol fatty acid esters, polyglyceryl fatty acid esters, polyglyceryl-3 oleate, polyglyceryl-6 dioleate, polyoxyethylene glycerides, polyoxyethylene sorbitan fatty acid esters, polyoxyethylene vegetable oils, polyoxyethylene-polyoxypropylene block copolymers, polypropylene glycol, polypropylene glycol fatty acid esters, propyl acetate, propylene glycol, propylene glycol diacetate, propylene glycol esters of C8, propylene glycol esters of unsaturated fatty acids, propylene glycol laurate, propylene glycol oleate, sorbitan fatty acid esters, sorbitan monolaurate, sorbitan monooleate, t-butylmethyl ether, tetrahydofuran, transcutol, triacetin, tributylcitrate, triethylcitrate, vegetable oils, water, and acetic acid.

The solvent system selected is able to dissolve the active agent and additives at sufficient concentration at ambient or elevated temperatures to enable efficient processing. The anti-solvent system consists of one or more solvents, preferably water along with modifiers such as cosolvents, suspending agents, and/or pH modifiers. Other examples of anti-solvents include alcohols, ethers, acids and hydrocarbons. It is preferable that the solvent and anti-solvent system is miscible to allow mixing of the two. The solvent system must have adequate affinity for the solutes so that a uniform suspension forms.

The initial crystallization phase of the process involves the mixing of the solvent containing the active agent and additive(s) with the anti-solvent. It is of importance to select a system that enables formation of a uniform suspension to allow the formation of uniform mixed phase co-crystals.

The anti-solvent may be mixed with the first solution containing the active agent and additives by any suitable method. The anti-solvent may be added to the first solution to form a second solution. Alternatively, the first solution may be added to the anti-solvent to form a second solution. The mixing of the second solution may optionally involve stirring including, for example, through using a magnetic stirrer or other mechanical stirrer.

The solvent is important for the successful incorporation of the solutes and formation of the transient meta-stable fraction. The solvent is also important in determining the loading concentrations achieved for the active agent and additives.

The anti-solvent is important to allow successful initial crystallization of the active agent and additive(s) and in determining the physical properties of the resulting mixed phase co-crystalline suspension and powder.

The mixed phase co-crystals can be isolated by conventional filtration methods, centrifugation or sedimentation. Removal of bulk solvent and anti-solvent components can be performed by washing the isolated solid. Preferably, the isolated mixed phase co-crystals are dried under vacuum at ambient or elevated temperature. The dried powder is then deaggregated using a milling or sieving process.

The additive(s) for use in the inventive methods and compositions include any suitable additives.

Additives, such as crystal lattice modifiers, can be added to the first solution. These modifiers must be acceptable for pharmaceutical or the intended use and usually are solids at room temperature. Examples of crystal lattice modifiers include, but are not limited to, fatty acids, fatty alcohols, PEG esters, PEG ethers, cellulose derivatives, pectins, glycerides, fatty esters, waxes, ethers, polyols, cyclodextrins (alpha, beta and gamma), hydroxypropyl-beta-cyclodextrin, sorbitan esters, propylene glycol esters, acetylated proteins, stearols, polyesters, polyvinylpyrrolidones, polyethylene glycols, triglycerides, cellulose acetates and sugar esters. Preferably, the crystal lattice modifier is selected from the group consisting of acetylated glycerol fatty acid esters, acetylated monoglycerides, acetylated monoglycerides of $C_6$ to $C_{20}$ fatty acids, alkylgluceosides, alkylmaltosides, bile salts, cholesterol, corn oil, diglycerides of $C_6$ to $C_{20}$ fatty acids, ethyl linoleate, ethyl oleate, fatty acid salts, saturated fatty acids, unsaturated fatty acids, fatty alcohols, fractionated cocoanut oil, glycerol fatty acid esters, glyceryl dicaprate, glyceryl dicaprylate, glyceryl dilaurate, glyceryl dioleate, glyceryl monocaprate, glyceryl monocaprylate, glyceryl monolaurate, glyceryl monooleate, isopropyl linoleate, isopropyl myristate, isopropyl palmitate, lactic acid conjugates of diglycerides, lactic acid conjugates of mono- and diglycerides, lactic acid conjugates of monoglycerides, lauric acid, lauryl macrogolglycenides, lower alcohol fatty acids esters, monoglycerides of a $C_6$ to $C_{20}$ fatty acids, myristic acid, oleic acid, palmitic acid, PEG 10-100 lionyl phenol series, PEG 1-4 stearate, PEG 15-100 octyl phenol series, PEG 20 dilaurate, PEG 20 glyceryl stearate, PEG 2-4 oleate, PEG 2-5 oleyl ether, PEG 3-16 castor oil, PEG 5-10 hydrogenated castor oil, PEG 5-20 soya sterol, PEG 6-20 almond oil, PEG 6-20 corn oil, PEG-10 laurate, PEG-100 stearate, PEG-12 laurate, PEG-12 oleate, PEG-15 stearate, PEG-2 cetyl ether, PEG-2 stearyl ether, PEG-20 almond oil, PEG-20 corn oil, PEG-20 dioleate, PEG-20 glyceryl laurate, PEG-20 glycidyl oleate, PEG-20 laurate, PEG-20 oleate, PEG-20 trioleate, PEG-200 oleate, PEG-24 cholesterol, PEG-25 glyceryl trioleate, PEG-25 phyto sterol, PEG-30 cholesterol, PEG-30 glyceryl laurate, PEG-30 glyceryl oleate, PEG-30 soya sterol, PEG-32 dilaurate, PEG-32 dioleate, PEG-32 distearate, PEG-32 laurate, PEG-32 oleate, PEG-35 castor oil, PEG-4 capric/caprylic triglyceride, mono, di, tri, tetra esters of vegetable oil and sorbitol, PEG-4 dilaurate, PEG-4 dioleate, PEG-4 distearate, PEG-40 castor oil, PEG-40 glyceryl laurate, PEG-40 hydrogenated castor oil, PEG-40 palm kernel oil, PEG-40 stearate, PEG-400 oleate, PEG-50 hydrogenated castor oil, PEG-6 caprate/caprylate glycerides, PEG-6 corn oil, PEG-6 dioleate, PEG-6 distearate, PEG-6 hydrogenated palm kernel oil, PEG-6 olive oil, PEG-6 palm kernel oil, PEG-6 peanut oil, PEG-6 sorbitan tetra, hexastearate, PEG-6 sorbitan tetraoleate, PEG-60 castor oil, PEG-60 corn oil, PEG-60 hydrogenated castor oil, PEG-8 caprate/caprylate glycerides, PEG-8 caprate/caprylate glycerides, PEG-8 dioleate, PEG-80 sorbitan laurate, pentaerythritol di, tetra stearate, isostearate, oleate, caprylate, or caprate, phospholipids, phosphoric acid polyoxymethylene alkylethers, phytosterol, poloxamer 188 (Pluronic® 68), poloxamers (Pluronics®), polyethylene glycol fatty acids esters, polyethylene glycol glycerol fatty acid esters, polyglyceryl 2-4 oleate, stearate, or isostearate, polyglyceryl 4-10 pentaoleate, polyglyceryl fatty acid esters, polyglyceryl fatty acid esters, fatty acids, polyglyceryl-10 laurate, polyglyceryl-10 trioleate, polyglyceryl-3 dioleate, polyglyceryl-3 distearate, polyglyceryl-3 oleate, polyglyceryl-6 dioleate, polyglyceryl-6 dioleate, polyoxyethylene alkyl ethers, polyoxyethylene alkylphenols, polyoxyethylene glycerides, polyoxyethylene hydrogenated vegetable oils, polyoxyethylene sorbitan fatty acid esters, polyoxyethylene sterols, polyoxyethylene vegetable oils, polyoxyethylene vegetable oils, polyoxyethylene hydrogenated vegetable oils, polyoxyethylene-polyoxypropylene block copolymers, polyoxyethylene-polyoxypropylene block copolymers, polypropylene glycol fatty acid esters, polysorbate 20, polysorbate 80, propylene glycol diglycerides, propylene glycol laurate, propylene glycol mono- or diesters of a $C_6$ to $C_{20}$ fatty acids fatty acids, propylene glycol oleate, reaction mixtures of polyols and at least one member selected from the group consisting of fatty acids, glycerides, vegetable oils, hydrogenated vegetable oils, and sterols, sesame seed oil, sorbitan fatty acid esters, sorbitan mono, trioleate, sorbitan mono, tristearate, sorbitan monoisostearate, sorbitan monolaurate, sorbitan monooleate, sorbitan monopalmitate, sorbitan monostearate, sorbitan sesquioleate, sorbitan sesquistearate, soybean oil, stearic acid, sterols, sucroglycerides, sucrose dipalmitate, sucrose distearate, sucrose monolaurate, sucrose monopalmitate, sucrose monostearate, sugar esters, sugar ethers, tocopheryl PEG-100 succinate, tocopheryl PEG-1000 succinate, transesteriefied vegetable oils, polysorbate 40 (Tween® 40), polysorbate 60 (Tween® 60) and mixtures thereof.

The crystal lattice modifiers are crystalline, semi-crystalline, amorphous, or ligands in form. The crystal lattice modifiers are not closely related to the active agent in chemical structure. They are typically soluble in the solvent system and insoluble in the anti-solvent system. These materials can be incorporated into the mixed phase co-crystal and will either decrease or increase the melting point of the mixed phase co-crystal relative to the active agent, but preferably reduce the melting point. Crystalline active agents will experience a reduction in melting point and broadening of the endotherm when observed with a differential scanning calorimeter (DSC). Depending on the application and the relative hydrophobicity of the active agent, the additive may increase or decrease the water solubility and wetability of the mixed phase co-crystal relative to the active agent. Depending on the application and the desired properties, the combined amount of crystal lattice modifiers may range widely in composition. It is desirable to co-crystallize more than one crystal lattice modifier with one or more active agents. Accordingly, the methods of the invention can comprise one or more crystal lattice modifiers.

It is possible to crystallize minor or low concentration additives along with the active agent(s) and crystal lattice modifier(s) of the mixed phase co-crystal composition. These additional additives can contribute to the formation of the mixed phase co-crystal particle and the addition of these additives then becomes integral to the particle structure. Examples of additional additives for use in the mixed phase co-crystal composition include modifiers, such as stabilizers and additives that impart specialized properties.

Modifiers, such as stabilizers, generally are incorporated into the mixed phase co-crystal at relatively low levels relative to the major component, with typical concentrations less than about 10% (e.g., about 9%, about 8%, about 7%, about 6%, about 5%, about 4%, about 3%, about 2%, about 1%) of the mixed phase co-crystal composition. Modifiers, such as stabilizers, are preferably crystalline solids soluble in the solvent system and insoluble in the anti-solvent system. Chemically these modifiers function as acids, bases, antioxidants, light protectants, viscosity modifiers, and/or surfactants.

Examples of acid modifiers for use in the invention include, but are not limited to, acetic acid, acrylic acid, adipic acid, alginic acid, alkanesulfonic acid, an amino acid, ascorbic acid, benzoic acid, boric acid, butyric acid, carbonic acid, citric acid, a fatty acid, formic acid, fumaric acid, gluconic acid, hydroquinosulfonic acid, hydrochloric acid, isoascorbic acid, lactic acid, maleic acid, methanesulfonic acid, oxalic acid, para-bromophenylsulfonic acid, phosphoric acid, propionic acid, p-toluenesulfonic acid, salicylic acid, stearic acid, succinic acid, tannic acid, tartaric acid, thioglycolic acid, toluenesulfonic acid, uric acid, and mixtures thereof.

Examples of base modifiers for use in the invention include, but are not limited to, ammonia, ethanolamine, diethanolamine, glucosamine, trolamine, sodium bicarbonate, potassium bicarbonate, sodium hydroxide, potassium hydroxide, TRIS, arginine, lysine, magnesium hydroxide, calcium hydroxide, sodium carbonate, potassium carbonate, ammonium bicarbonate, and mixtures thereof.

Examples of antioxidant modifiers for use in the invention include, but are not limited to, α-tocopherol, ascorbic acid, ascorbyl palmitate, BHT, BHA, malic acid, propyl gallate, and mixtures thereof.

Examples of viscosity modifiers for use in the invention include, but are not limited to, methylcellulose, ethylcellulose, acetylated gelatin, hydroxypropyl cellulose, hydroxypropyl methylcellulose, hydroxyethyl cellulose, hydroxypropyl methyl phthalate, polyvinyl acetate phthalate, sodium carboxymethylcellulose, agar, acacia, tragacanth, carrageen, pectins, polyvinylpyrrolidone, polyvinyl alcohol, polyvinyl acetate, xanthane gum, and mixtures thereof.

Examples of surfactant modifiers for use in the invention include, but are not limited to, acetylated glycerol fatty acid esters, acetylated monoglycerides, acetylated monoglycerides of $C_6$ to $C_{20}$ fatty acids, alkylgluceosides, alkylmaltosides, bile salts, cholesterol, corn oil, diglycerides of $C_6$ to $C_{20}$ fatty acids, ethyl linoleate, ethyl oleate, fatty acid salts, saturated fatty acids, unsaturated fatty acids, fatty alcohols, fractionated cocoanut oil, glycerol fatty acid esters, glyceryl dicaprate, glyceryl dicaprylate, glyceryl dilaurate, glyceryl dioleate, glyceryl monocaprate, glyceryl monocaprylate, glyceryl monolaurate, glyceryl monooleate, isopropyl linoleate, isopropyl myristate, isopropyl palmitate, lactic acid conjugates of diglycerides, lactic acid conjugates of mono- and diglycerides, lactic acid conjugates of monoglycerides, lauric acid, lauryl macrogolglycenides, lower alcohol fatty acids esters, monoglycerides of a $C_6$ to $C_{20}$ fatty acids, myristic acid, oleic acid, palmitic acid, PEG 10-100 lionyl phenol series, PEG 1-4 stearate, PEG 15-100 octyl phenol series, PEG 20 dilaurate, PEG 20 glyceryl stearate, PEG 2-4 oleate, PEG 2-5 oleyl ether, PEG 3-16 castor oil, PEG 5-10 hydrogenated castor oil, PEG 5-20 soya sterol, PEG 6-20 almond oil, PEG 6-20 corn oil, PEG-10 laurate, PEG-100 stearate, PEG-12 laurate, PEG-12 oleate, PEG-15 stearate, PEG-2 cetyl ether, PEG-2 stearyl ether, PEG-20 almond oil, PEG-20 corn oil, PEG-20 dioleate, PEG-20 glyceryl laurate, PEG-20 glycidyl oleate, PEG-20 laurate, PEG-20 oleate, PEG-20 trioleate, PEG-200 oleate, PEG-24 cholesterol, PEG-25 glyceryl trioleate, PEG-25 phyto sterol, PEG-30 cholesterol, PEG-30 glyceryl laurate, PEG-30 glyceryl oleate, PEG-30 soya sterol, PEG-32 dilaurate, PEG-32 dioleate, PEG-32 distearate, PEG-32 laurate, PEG-32 oleate, PEG-35 castor oil, PEG-4 capric/caprylic triglyceride, mono, di, tri, tetra esters of vegetable oil and sorbitol, PEG-4 dilaurate, PEG-4 dioleate, PEG-4 distearate, PEG-40 castor oil, PEG-40 glyceryl laurate, PEG-40 hydrogenated castor oil, PEG-40 palm kernel oil, PEG-40 stearate, PEG-400 oleate, PEG-50 hydrogenated castor oil, PEG-6 caprate/ caprylate glycerides, PEG-6 corn oil, PEG-6 dioleate, PEG-6 distearate, PEG-6 hydrogenated palm kernel oil, PEG-6 olive oil, PEG-6 palm kernel oil, PEG-6 peanut oil, PEG-6 sorbitan tetra, hexastearate, PEG-6 sorbitan tetraoleate, PEG-60 castor oil, PEG-60 corn oil, PEG-60 hydrogenated castor oil, PEG-8 caprate/caprylate glycerides, PEG-8 caprate/caprylate glycerides, PEG-8 dioleate, PEG-80 sorbitan laurate, pentaerythritol di, tetra stearate, isostearate, oleate, caprylate, or caprate, phospholipids, phosphoric acid polyoxymethylene alkylethers, phytosterol, Pluronic F68, Pluronics, poloxamers, polyethylene glycol fatty acids esters, polyethylene glycol glycerol fatty acid esters, polyglyceryl 2-4 oleate, stearate, or isostearate, polyglyceryl 4-10 pentaoleate, polyglyceryl fatty acid esters, polyglyceryl fatty acid esters, fatty acids, polyglyceryl-10 laurate, polyglyceryl-10 trioleate, polyglyceryl-3 dioleate, polyglyceryl-3 distearate, polyglyceryl-3 oleate, polyglyceryl-6 dioleate, polyglyceryl-6 dioleate, polyoxyethylene alkyl ethers, polyoxyethylene alkylphenols, polyoxyethylene glycerides, polyoxyethylene hydrogenated vegetable oils, polyoxyethylene sorbitan fatty acid esters, polyoxyethylene sterols, polyoxyethylene vegetable oils, polyoxyethylene vegetable oils, polyoxyethylene hydrogenated vegetable oils, polyoxyethylene-polyoxypropylene block copolymers, polyoxyethylene-polyoxypropylene block copolymers, polypropylene glycol fatty acid esters, polysorbate 20, polysorbate 80, propylene glycol diglycerides, propylene glycol laurate, propylene glycol mono- or diesters of a $C_6$ to $C_{20}$ fatty acids fatty acids, propylene glycol oleate, reaction mixtures of polyols and at least one member selected from the group consisting of fatty acids, glycerides, vegetable oils, hydrogenated vegetable oils, and sterols, sesame seed oil, sorbitan fatty acid esters, sorbitan mono, trioleate, sorbitan mono, tristearate, sorbitan monoisostearate, sorbitan monolaurate, sorbitan monooleate, sorbitan monopalmitate, sorbitan monostearate, sorbitan sesquioleate, sorbitan sesquistearate, soybean oil, stearic acid, sterols, sucroglycerides, sucrose dipalmitate, sucrose distearate, sucrose monolaurate, sucrose monopalmitate, sucrose monostearate, sugar esters, sugar ethers, tocopheryl PEG-100 succinate, tocopheryl PEG-1000 succinate, transesteriefied vegetable oils, Tween 40, Tween 60, and mixtures thereof. Examples of stabilizers include BHA, BHT, Vitamin E, Vitamin C, titanium oxide, acetic acid, benzoic acid, glycine, arginine, monoethanolamine, N-glucosamine, methysulfonic acid, maleic acid and UV blockers.

Other additives can be incorporated in the mixed phase co-crystal particle to impart specialized properties, such as improved intestinal membrane permeability, resistance toward enzymatic bioconversion, bioadhesion, etc. Examples of these include caprylic acid, oleic acid, bile salts, PEG ethers, grapefruit extract, niacin, cellulose derivatives, silicon dioxide, starch and the like.

Figure 1B:
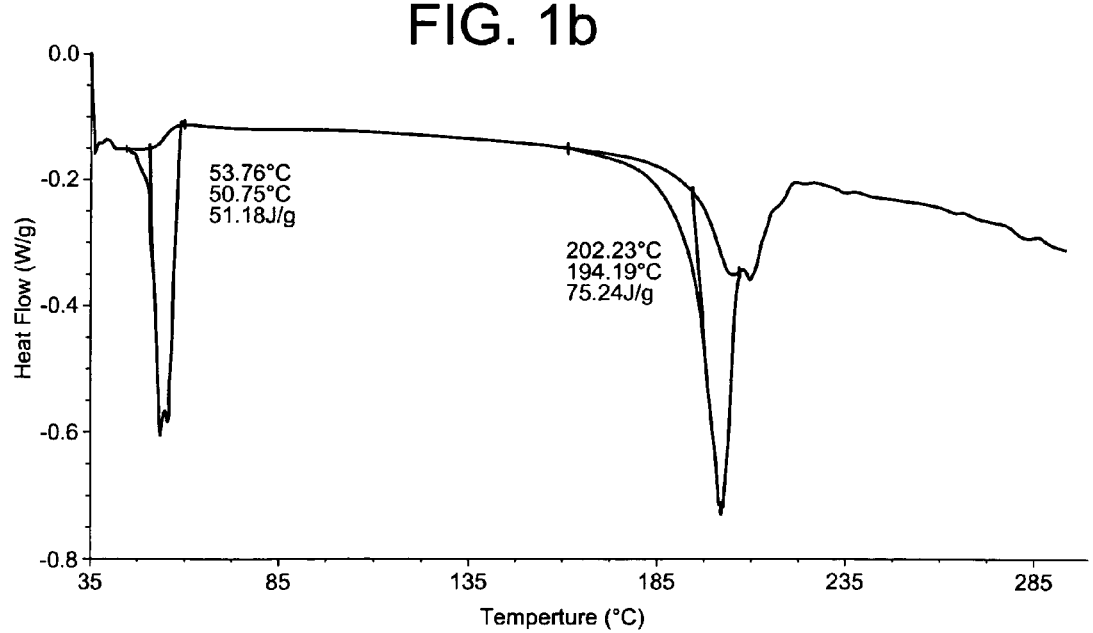
FIG. 1B is a graph showing heat flow to temperature of a mixed phase co-crystal wherein the active agent is hydrocortisone acetate.
Figure 2A:
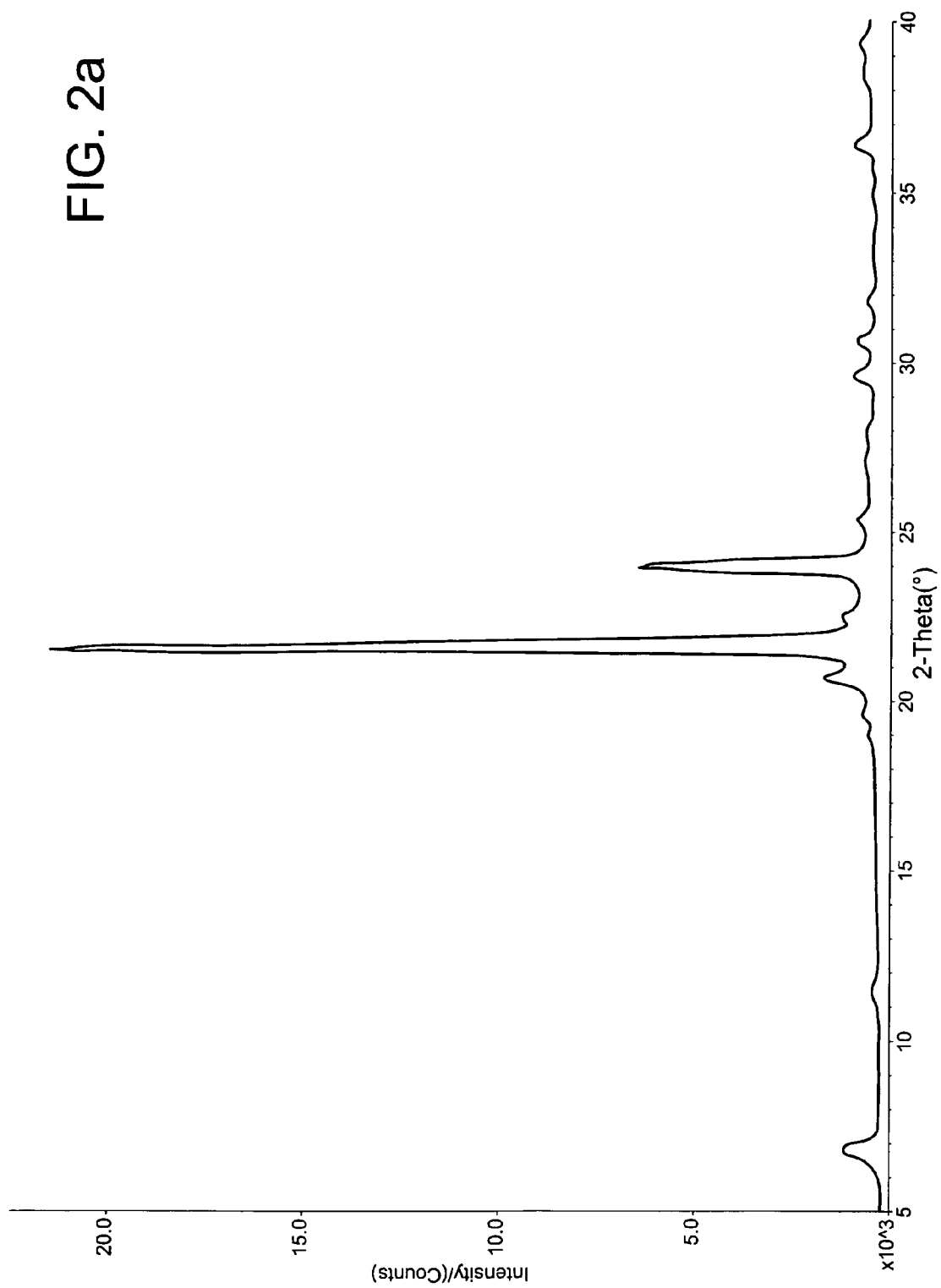
FIG. 2A is a graph of an x-ray diffraction (XRD) pattern of pure stearic acid.
Figure 2C:
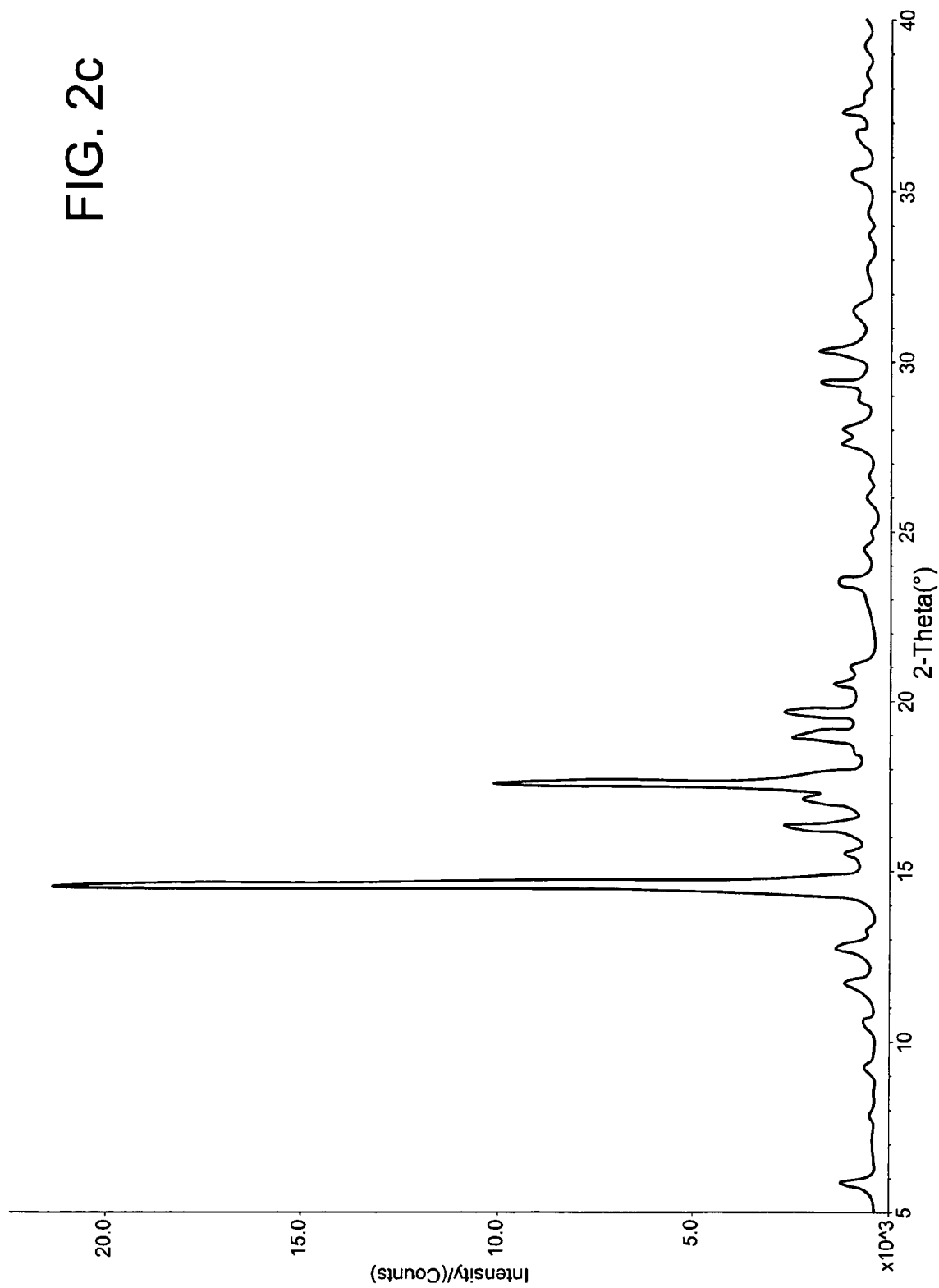
FIG. 2C is a graph of an XRD pattern of pure active agent (hydrocortisone).

Distinguishing properties of the mixed phase co-crystal include the preservation of the crystal form of the active agent(s), reduced crystallinity of the active agent, preservation of the crystalline form of the additive and enhanced physical properties of the mixed phase co-crystal powder. For instance, in the case of reduced crystallinity of the active agent, the active agent shows a small reduction in melting point and broadening of the endotherm (FIGS. 1A and 1B). This is brought about by the co-crystallization of the crystal lattice modifier in the active crystal lattice, hence an apparent reduction of crystallinity. The presence of the Additive Phase is shown by the presence of a characteristic melting point or endotherm in the DSC. The existence of both active and Additive Phases is also evident in the x-ray diffraction (XRD) pattern of the mixed phase co-crystal powder (FIG. 2). A reduction in the signal to noise ratio in the XRD pattern is another indicator of reduced crystallinity of the active agent in mixed phase co-crystal powders (FIG. 3).

In Tables 1, 2, 4, 6, and 7, a reduction in melting point of the mixed phase co-crystal composition as compared with the pure active agent (API) is observed. This is an indication of reduced crystallinity of the active agent brought about by the co-crystallization of the modifiers with the active agent.

In Tables 2, 6, and 7, a reduction in enthalpy in the mixed phase co-crystal composition as compared to the pure active agent is observed. This is also an indication of reduced crystallinity of the active agent brought about by the co-crystallization of the modifiers with the active agent.

Figure 4:
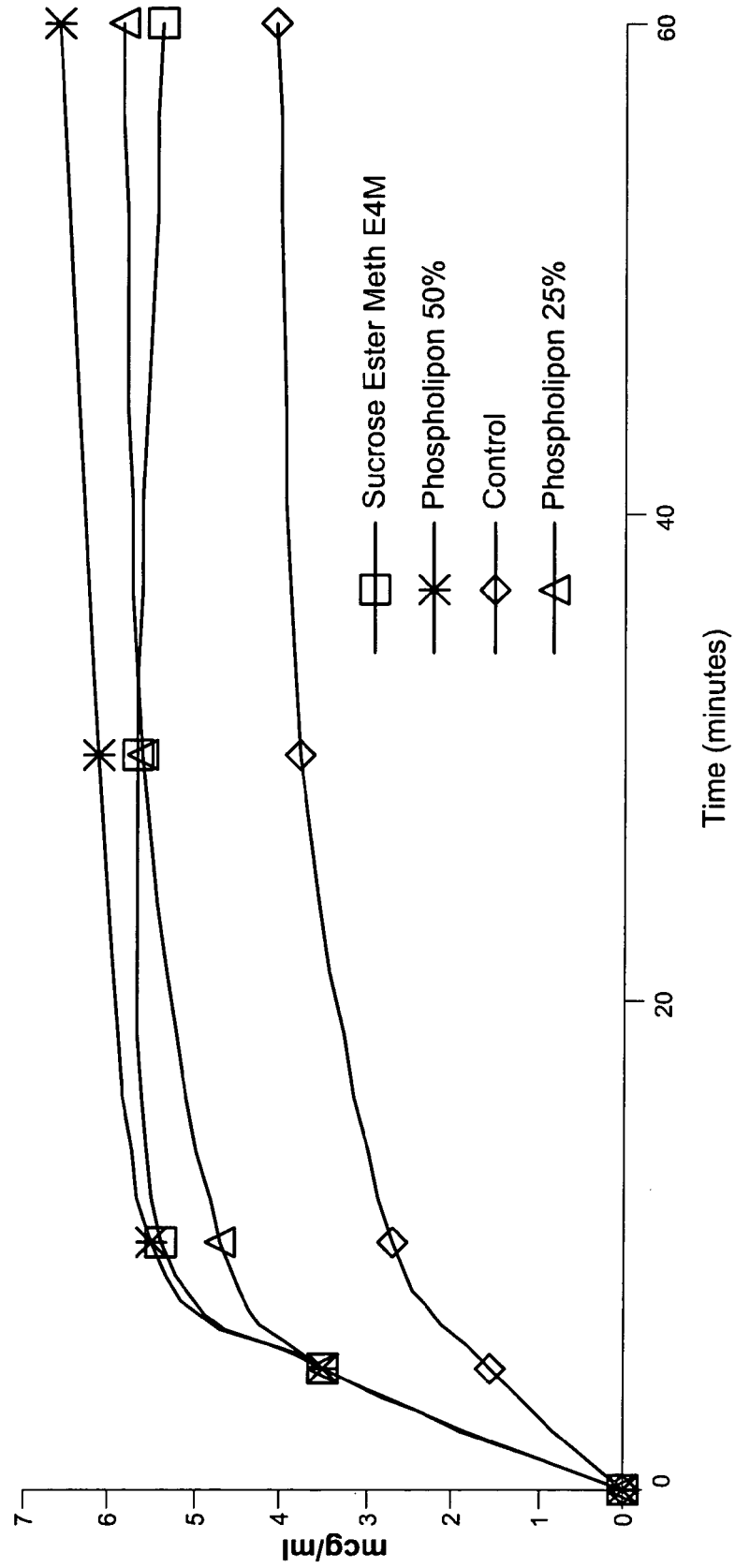
FIG. 4 is a graph comparing dissolution profiles (mcg/mL over time) of mixed phase co-crystals of cyclosporin prepared using the method described in Example 4.

In Tables 1, 2, 3, 4, 6, and 7, an increase of water solubility as compared to the active agent is obtained for the mixed phase co-crystalline materials shown in these tables. This illustrates the distinguishing property for improvement of water solubility of the mixed phase co-crystal composition of the invention. Another distinguishing property is improvement of dissolution of the active agent as shown in Table 5 and FIGS. 4, 5, and 6.

The formulated mixed phase co-crystalline material can be directly incorporated in a pharmaceutically acceptable dosage form as part of the formulation process without prior isolation of the mixed phase co-crystalline particles. This requires that all the solvents, anti-solvents and crystal modifiers are GRAS materials, listed in major pharmacopeas or are found as inactive ingredients in pharmaceutical dosage forms. The solvent and anti-solvents must be volatile or can remain as a component of the dosage form. Should the solvent/anti-solvents remain in the dosage form they must be pharmaceutically acceptable and have prior use in pharmaceutical dosage forms found in commerce (references: USP, EP, PDR and FDA Inactive Ingredient List).

Alternatively, mixed phase co-crystals can be isolated by filtration, sedimentation or centrifugation. The isolated material can then be washed with water and dried with the aid of heat or vacuum.

The process used in preparation of the mixed phase co-crystalline material utilizes one or more volatile solvents/anti-solvents that are removed during a drying step of the process. This can be accomplished by several methods commonly used for processing pharmaceutical dosage forms. These can include combining the crystallized mixed phase co-crystalline material suspended in the solvent/anti-solvent system with a pharmaceutically acceptable bulking agent. The volatile solvent/anti-solvent is removed by drying the resulting granulation containing the formulated mixed phase co-crystal and bulking agent(s). Alternatively, the solvent system can be combined with the bulking agent and the volatile solvents removed through evaporation without prior crystallization of the mixed phase co-crystalline material.

Any suitable bulking agent can be used. Preferably, the bulking agent is a pharmaceutically acceptable bulking agent. Examples of suitable bulking agents include, but are not limited to, microcrystalline cellulose, lactose anhydrous, lactose monohydrate, sucrose, mannitol, maltitol, sorbitol, calcium phosphate, calcium sulfate, starch, pregelatinized starch, silica, powdered cellulose, croscarmollose, bentonite, kaolin, magnesium aluminum silicate, dextrins, amylose, glucose, ethylcellulose, hydroxyethyl cellulose, hydroxymethyl cellulose, hydroxypropylmethyl cellulose, maltodextrin, povidone, calcium carbonate, compressible sugar, cyclodextrins, dextran, talc, sodium starch glycolate, gelatin, magnesium carbonate, magnesium oxide, maltitol, methylcellulose, xylitol, and carbomer.

Preferred examples of the bulking excipient include pharmaceutically acceptable powders that are generally recognized as safe (GRAS) or listed in major Pharmacopeas. Examples of powders include cellulosic materials (microcrystalline cellulose and hydroxypropylcellulose), polyvinylpyrrolidones (PVP and crospovidone), sugars (lactose and sucrose), starches (pregelatined starch and corn starch), inorganic salts (dicalcium phosphate and calcium sulfate) and reduced sugars (mannitol and sorbitol).

Preferred methods for removing the volatile solvents utilize a fluid bed spray granulation, spray drying, or vacuum granulating/drying processes. The resulting powder or granulation is sized to an average particle size in the range of 50 to 300 microns in size (e.g., about 75 microns, about 100 microns, about 125 microns, about 150 microns, about 175 microns, about 200 microns, about 225 microns, about 250 microns, about 275 microns, or ranges thereof) which is suitable for further powder blending and subsequent dosage form manufacture by encapsulation into hard gelatin capsules, tablets, or other dosage forms.

A second alternative process for mixed phase co-crystal formation utilizes a volatile solvent system that has sufficient solvent capacity to dissolve the active agent and modifiers. The mixed phase co-crystals are formed by precipitation with a non-solvent system using materials that are ingestable (GRAS) and can be formulated as a fill for soft gelatin and 2-piece hard gelatin capsules. Examples of these liquids include triglycerides (sesame oil, soybean oil and fractioned cocoanut oil), propylene glycol esters, fatty acids (oleic acid, caprylic acid and myristic acid), polyethylene glycols (PEG 400, PEG 600, PEG 3350, etc.), mixed phase glycerides (Gelucires, Labrasol and Labrafils), PEG esters, polysorbates, glycerin, polyol solutions (sorbitol, mannitol, maltose, etc), water, and other pharmaceutically acceptable oils. In this case, the volatile solvent/anti-solvents are removed partially or completely after crystallization of the mixed phase co-crystalline particles with the aid of a carrier gas, vacuum, and/or application of heat. Sparging of the resulting suspension with a carrier gas such as nitrogen or compressed air is the preferred method when a carrier gas is used. The mixed phase co-crystal preparation results in a suitable suspension for encapsulation as anoil based or hydrophilic based fill formulation as soft gelatin or hard gelatin capsules.

The present invention provides methods for formulation of mixed phase co-crystals that include initial crystallization of the active agent along with additive(s) and subsequent transformation to the mixed phase co-crystal form(s) or by evaporation of volatile solvents containing the co-crystalline components. The ratio or composition of the components can be varied and produced in a wide range. The composition of the mixed phase co-crystal form and the extent of co-crystallization achieved will determine the specific physical properties. Thus, it is possible to formulate a mixed phase co-crystal with the desired properties based on the nature of the additive(s) and the composition of the additive(s) incorporated. It has been discovered that the desired properties can be optimized through the use of carefully balanced components that are co-crystallized with the active agent(s).

In a preferred embodiment of the invention, the solvent and anti-solvent are substantially removed from the mixed phase crystalline material, such that the mixed phase crystalline material is a dry powder suitable for direct encapsulation or tableting.

The inventor discovered that mixed phase co-crystals can improve the inherent properties of active agents that enable the successful development of delivery systems for the active agents. These mixed phase co-crystalline materials can be incorporated in a formulation while being formed as part of the dosage form processing steps.

In a preferred embodiment, the mixed phase co-crystal composition comprises a mixed phase co-crystal of an active agent and at least one crystal lattice modifier, wherein the content of the active agent ranges from about 5% to 95% (e.g., about 10%, about 15%, about 20%, about 25%, about 30%, about 35%, about 40%, about 45%, about 50%, about 55%, about 60%, about 65%, about 70%, about 75%, about 80%, about 85%, or ranges thereof) by weight of the total weight of the material, and wherein the crystal lattice modifier ranges from 2% to 95% (e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or ranges thereof). Preferably, the crystal lattice modifier ranges from 10% to 40% by weight for each individual modifier of the total weight of the material.

The following examples further illustrate the invention but, of course, should not be construed as in any way limiting its scope. The examples do not constitute the entire range of active agents or crystal lattice modifiers that may be used.

Example 1

This example demonstrates a method to prepare mixed phase co-crystals of hydrocortisone.

|   | Ingredients | Amount |
|---|---|---|
| 1 | Hydrocortisone (Pharmacia-Upjohn) | 300 mg |
| 2 | Sorbitan monopalmitate (ICI) | 100 mg |
| 3 | Dimethyl sulfoxide | 1.6 mL* |
| 4 | Deionized water | 8.0 mL* |

*Removed

The mixed phase co-crystals of hydrocortisone were prepared by dissolving the active gent (hydrocortisone; Pharmacia-Upjohn) and a crystal lattice modifier (sorbitan monopalmitate; ICI) in dimethyl sulfoxide (DMSO, Fisher) with the application of heat (ca. 60° C.) and vortex mixing. The resulting solution was added gradually over a period of 5 minutes to deoinoized water at 30 to 40° C. while being vortex mixed or stirred with a magnetic stir bar. The precipitation that forms was mixed for 1 to 2 hours at 30 to 40° C. The reactive mixture was allowed to cool to room temperature and gently mixed for an additional 12 to 48 hours. The resulting mixed phase co-crystal product was collected with a Buchner funnel using a Whatman paper filter. The filter cake was repeatedly washed with additional water and dried under vacuum at 25° C. for 1 or more days.

Example 2

This example demonstrates a method of preparing mixed phase co-crystals of hydrocortisone.

|   | Ingredients | Amount |
|---|---|---|
| 1 | Hydrocortisone | 300 mg |
| 2 | Cetostearyl alcohol | 84 mg |
| 3 | Methocel E4M (as 2% solution in DMSO*) | 800 mg |
| 4 | N-methylpyrrolidone | 1.6 ml* |
| 5 | Deionized water | 8.0 mL* |

*Removed

To prepare the mixed phase co-crystals, hydrocortisone (Pharmacia Upjohn) and cetostearyl alcohol (Croda) were dissolved in N-methylpyrrolidone (ISP Technologies) with the application of heat (ca. 60° C.) and vortex mixing. These ingredients were added to 800 mg of a 2% solution of Methocel E4M (methylcellulose) in DMSO and mixed with until dissolved. The resulting solution was added gradually over a period of 5 minutes to 8.0 mL of deionized water at 30 to 40° C. while being vortex mixed or stirred with a magnetic stir bar. The precipitation that formed was mixed for 1 to 2 hours at 30 to 40° C. The reaction mixture was allowed to cool to room temperature and gently mixed for an additional 12 to 48 hours. The resulting mixed phase co-crystal product was collected with a Buchner funnel using a Whatman paper filter. The filter cake was repeatedly washed with additional water and dried under vacuum at 25° C. for 1 or more days.

Example 3

This example demonstrates a method of preparing mixed phase co-crystals of hydrocortisone acetate.

|   | Ingredients | Amount |
|---|---|---|
| 1 | Hydrocortisone acetate | 320 mg |
| 2 | Methocel E4M (as 2% solution in DMSO*) | 200 mg |
| 3 | Sorbitan monostearate | 4 mg |
| 4 | Stearic acid | 4 mg |
| 5 | Cetostearyl alcohol | 4 mg |
| 6 | Lanolin | 4 mg |
| 7 | Dimethyl sulfoxide | 1.6 mL* |
| 8 | Deionized water | 8.0 mL* |

*Removed

To prepare the mixed phase co-crystals, hydrocortisone acetate (Pharmacia-Upjohn), sorbitan monostearate (ICI), stearic acid (Croda), cetostearyl alcohol (Croda), lanolin (Croda) were dissolved in dimethyl sulfoxide with the application of heat (ca. 60° C.) and vortex mixing. 200 mg of a 2% solution of Methocel E4M (methylcellulose) in DMSO was added and mixed with the previous ingredients until dissolved. The resulting solution was added gradually over a period of 5 minutes to the water at room temperature while being vortex mixed or stirred with a magnetic stir bar. The precipitation that formed was gently mixed for an additional 12 to 48 hours. The resulting mixed phase co-crystal product was collected with a Buchner funnel using Whatman paper filter. The filter cake was repeatedly washed with additional water and dried under vacuum at 25° C. for 1 or more days.

Example 4

This example demonstrates a method of preparing mixed phase co-crystals of cyclosporin.

|   | Ingredients | Amount |
|---|---|---|
| 1 | Cyclosporin (Gallipot) | 40 mg |
| 2 | Crotein ADW (10% in ethanol*) | 100 µL |
| 3 | Sorbitan monostearate | 1 mg |
| 4 | Lanolin | 1 mg |
| 5 | Stearic acid | 1 mg |
| 6 | Compritol 888 ATO | 1 mg |
| 7 | N-methylpyrrolidone | 0.2 mL* |
| 8 | Deionized water | 1.0 mL* |

*Removed

To prepare the mixed phase co-crystals, cyclosporin (Gallipot), Crotein ADW (AMP-Isostearoyl Hydrolyzed Wheat Protein; 10% in ethanol), sorbitan monostearate, lanolin (Croda), stearic acid, and Compritol 888 ATO (glycerol behenate; Gattefosse) were dissolved in N-methylpyrrolidone (ISP) with the application of heat (ca. 60° C.) and vortex mixing. 1.0 mL of deionized water was added to this solution was added and the resulting reaction mixture was vortexed at room temperature. The reaction mixture was agitated at room temperature for 18 to 48 hours. The resulting mixed phase co-crystal product was collected with a Buchner funnel using Whatman paper filter. The filter cake was repeatedly washed with additional water and dried under vacuum at 25° C. for 1 or more days.

Example 5

This example demonstrates a method of preparing mixed phase co-crystals of itraconazole.

|   | Ingredients | Amount |
|---|---|---|
| Part A: | | |
| 1 | Itraconazole (Spectrum) | 300 mg |
| 2 | Crodesta F160 (Croda) | 50 mg |
| 3 | Crodacid (Croda) | 50 mg |
| 4 | DMSO* | 900 mg |
| 5 | Urea | 200 mg |
| 6 | N-methylpyrrolidone | 800 mg |
| Part B: | | |
| 7 | Urea | 4000 mg |
| 8 | Deionized water* | 4000 mg |

*Removed

To prepare the mixed phase co-crystals, Crodesta F160 (sucrose stearate) and Crodacid (behenic acid) were dissolved in DMSO. Urea was dissolved in N-methylpyrrolidone with heating. The resulting solutions were combined, and itraconazole (Spectrum) was added and dissolved with heat, completing Part A solution.

Part B solution was prepared by dissolving urea in water with heating, then allowing the solution to cool to room temperature. The Part A solution was then added to Part B by slow addition with mixing, forming a precipitate. The resulting suspension was gently vortexed at room temperature for 2 days. The mixed phase co-crystals were isolated by filtration, washed with a small aliquot of water, and dried at 40° C. in an oven.

Example 6

This example demonstrates a method of preparing mixed phase co-crystals of itraconazole.

|   | Ingredients | Amount |
|---|---|---|
| 1 | Itraconazole | 5000 mg |
| 2 | Stearth-20 (Croda) | 2500 mg |
| 3 | Pluronic F-68 | 2500 mg |
| 4 | Ethanol* | 200 mL |
| 5 | Refined soybean oil | 100 mL |

*Removed

To prepare the mixed phase co-crystals, itraconazole, Stearth-20, and Pluronic F-68 (Poloxamer 188) were dissolved in hot ethanol (>70° C.) with mixing and maintained at this temperature. The hot ethanol solution was added gradually to the soybean oil that was kept cool (0 to 10° C.) with vigorous mixing. The resulting suspension of the mixed phase co-crystals was stirred while compressed air was bubbled through the suspension at room temperature until the residual alcohol was reduced to less than 10% by weight as determined by loss on drying at 105° C. This prepared suspension was then encapsulated into hard gelatin and soft gelatin capsules.

Example 7

This example demonstrates a method of preparing mixed phase co-crystals of nimodipine.

|   | Ingredients | Amount |
|---|---|---|
| 1 | Nimodipine (Lusochimica) | 300 mg |
| 2 | Capmul GMS (Croda) | 5 mg |
| 3 | Compritol 888 ATO (Croda) | 5 mg |
| 4 | Crodacid B (Croda) | 5 mg |
| 5 | Solutol HS 15 (BASF) | 5 mg |
| 6 | Dimethyl sulfoxide | 1.0 mL* |
| 7 | N-methylpyrrolidone | 800 mg* |
| 8 | Deionized water | 1.0 mL* |

*Removed

To prepare the mixed phase co-crystals, nimodipine, Capmul GMS (glycerol momostearate), Compritol 888 ATO (glycerol behenate), Crodacid B (behenic acid), and Solutol HS 15 (PEG 660 hydroxystearate) were dissolved in N-methylpyrrolidone and DMSO with the application of heat (ca. 60° C.) and vortex mixing. The resulting solution was added gradually over a period of 5 minutes to deionized water at room temperature, while being vortex mixed or stirred with a magnetic stir bar. The precipitation that formed was gently mixed for an additional 12 to 48 hours. The resulting mixed phase co-crystal product was collected with a Buchner funnel using Whatman paper filter. The filter cake was repeatedly washed with additional water and dried under vacuum at 25° C. for 1 or more days.

Example 8

This example demonstrates a method of preparing mixed phase co-crystals (Batch No. F833-025B of FIG. 6) of progesterone.

|   | Ingredients | Amount |
|---|---|---|
| 1 | Progesterone (Pharmacia-Upjohn) | 2000 mg |
| 2 | Pluronic F68 (BASF) | 600 mg |
| 3 | Methocel E15 | 300 mg |
| 4 | Ethanol* | 2.0 mL |
| 5 | Soybean oil | 3.0 mL |
| 6 | Miglyol 810 | 3.0 mL |

*Removed

To prepare the mixed phase co-crystals, progesterone, Pluronic F68 (Poloxamer 188) and Methocel E15 (hydroxypropylmethyl cellulose) were dissolved in ethanol (>70° C.). Soybean oil and Miglyol 810 (glycerol tri-caprylate/caprate) were mixed at 5° C., and then the warm ethanol solution was added and mixed. The resulting suspension is mixed at 5° C. for 2 hours. Compressed air was sparged through the oil suspension at room temperature to evaporate the ethanol for approximately 18 hours. The resulting suspension was ground or sieved to a smooth consistency and encapsulated in hard gelatin capsules. A scaled up version of the same formulation was encapsulated in soft gelatin capsules.

Example 9

This example demonstrates a method of preparing mixed phase co-crystals of progestrone.

|   | Ingredients | Amount |
|---|---|---|
| Part A: | | |
| 1 | Progesterone (Pharmacia-Upjohn) | 40.0 g |
| 2 | Sucrose monostearate | 12.0 g |
| 3 | Pharmacoat 603 | 6.0 g |
| 4 | Ethanol (200 proof)* | 50 g |
| 5 | Purified water* | 200 g |
| Part B: | | |
| 6 | Part A suspension | 308 g |
| 7 | Lactose, hydrous | 400 g |

*Removed

To prepare the mixed phase co-crystals, progesterone, sucrose monostearate, and Pharmacoat 603 (hydroxypropylmethyl cellulose) were dissolved in ethanol (>70° C.). The hot ethanol solution was gradually added to the purified water (5° C.) and mixed. The resulting suspension was mixed at room temperature for 2 hours. The suspension then was passed through a 30-mesh screen and sprayed onto the lactose in a fluid bed drier. The final dried granulation was then encapsulated into a two-piece hard gelatin capsule.

Example 10

This example demonstrates that mixed phase co-crystals prepared by the methods of the invention have beneficial properties.

Four lots of mixed phase co-crystal formulations were prepared by the method described in Example 8 using the following compositions:

|   |   | Amount Batch No. | | | |
|---|---|---|---|---|---|
|   | Ingredients | F-833-025B | F-833-023C | F-833-024A | F-833-025A |
| 1 | Progesterone (Pharmacia-Upjohn) | 2000 mg | 1000 mg | 1000 mg | 2000 mg |
| 2 | Pluronic F68 (Poloxamer 188) | 600 mg | 300 mg | 300 mg | 600 mg |
| 3 | Methocel E15 (Hydroxypropylmethyl Cellulose) | 300 mg | — | — | — |
| 4 | Stearth 20 | — | — | 300 mg | — |
| 5 | Ethanol* | 2.0 mL | 1.0 mL | 1.0 mL | 2.0 mL |
| 6 | PVP K30 (Polyvinylpyrrolidone) | — | — | — | 300 mg |
| 7 | Soybean oil | 3.0 mL | 1.5 mL | 1.5 mL | 3.0 mL |
| 8 | Miglyol 810 (Glycerol Tri-caprylate/Caprate) | 3.0 mL | 1.5 mL | 1.5 mL | 3.0 mL |

*Removed

FIG. 6 illustrates a comparison of in vitro dissolution results for the four lots of mixed phase co-crystal formulations (F833-023c, -024A, -025A and -025B) containing progesterone as the active ingredient as compared to commercial Prometrium 200 mg softgel capsules from two batches. The dissolution method used USP apparatus I, paddles at 50 rpm, 27° C., and media of isopropyl alcohol: water (1:1). Progesterone was analyzed via HPLC. Each of the mixed phase co-crystal formulations showed an increased rate of dissolution as compared to the commercial progesterone capsules (FIG. 6).

Thus, mixed phase co-crystal formulations prepared by the methods of the invention demonstrate improved properties, such as dissolution rate.

Example 11

This method demonstrates a method of preparing mixed phase co-crystals of progesterone.

|   | Ingredients | Amount |
|---|---|---|
| 1 | Progesterone (Pharmacia-Upjohn) | 20.0 g |
| 2 | Pluronic F68 (Poloxamer 188) | 6.0 g |
| 3 | Methocel E15 (Hydroxypropyl Methylcellulose) | 3.0 g |
| 4 | Ethanol (200 proof)* | 80 g |
| 5 | Purified water* | 150 g |

*Removed

To prepare the mixed phase co-crystals, progesterone, Pluronic F68 (Poloxamer 188), and Methocel E15 (hydroxypropyl methylcellulose) were dissolved in hot ethanol (boiling temperature). This solution was gradually added over a period of 20 minutes to water at 5° C. while mixing. After the initial crystallization of the mixed phase co-crystal material, mixing was continued for an additional 2 hours at 5° C. The suspension was allowed to remain at room temperature for 24 hours. The mixed phase co-crystals were isolated by filtration, washed with additional water, and dried at 40° C.

Photomicrographs were taken with a polarizing microscope at 100× magnification after different time points in the manufacture of the mixed phase co-crystals. An image taken immediately after the addition of the alcohol solution illustrated that large needle-like crystals and large plate-like crystals had formed. These crystal forms were transient and, therefore, were kinetically favored products. These crystal forms gradually converted with time to the thermodynamically favored mixed phase co-crystals that were smaller in size and of uniform morphology, as observed in photomicrographs taken 1 hour and 2 hours after mixing at 5° C.

Example 12

This example demonstrates the physical properties of various mixed phase co-crystal materials produced by the methods of the invention.

Tables 1 and 2 demonstrate the physical properties of mixed phase co-crystals of hydrocortisone and hydrocortisone acetate, respectively. To prepare the mixed phase co-crystals of Tables 1 and 2, the active agent and crystal lattice modifiers were dissolved in DMSO or n-methyl-pyrrolidone or a blend of the two with gentle heating (60° C.) and vortex mixing. The resulting solution was combined with water to intiate the crystallization of the mixed phase co-crystals and vortexed for 18 to 48 hours at room temperature. The mixed phase co-crystals were isolated by filtration, washed with water, and dried.

Gelucire 44/14 refers to lauroyl macrogol-32 glycerides; Ethocel refers to ethylcellulose resin; Emucire refers to cetyl alcohol (and) ceteth-20 (and) steareth-20; Methocel E3 refers to hydoxypropyl methylcellulose; and Suppircire refers to a blend of mono-, di-, and tri-glycerides.

TABLE 1

Physical Properties of Hydrocortisone Mixed Phase Co-Crystals

| Co-crystal Lot No. | Description | Melting Point(s)* (° C.) | Water Solubility (mcg/mL) | Assay (% w/w) |
|---|---|---|---|---|
| Control (Intact API) | Hydrocortisone (HC) | 240–242 | 302 | 100 |
| DG-5B | 20% Stearic Acid | 180–188 | 318 | 87 |
| DG-27 | 20% Cetostearyl Alcohol | 185–195 | 319 | 80 |
| DG-45A | 10% Sorbitan Monopalmitate | 186–191 | 376 | 87 |
| DG-45C | 30% Sorbitan Monopalmitate | 179–187 | 375 | 77 |
| DG-60a | 25% Sorbitan Monopalmitate | 174–182 | 530 | 81 |
| dg-60b | 21% Sorbitan Monopalmitate, 4% Methocel E4M | 170–180 | 660 | 81 |
| dg-60c | 21% Sorbitan Monopalmitate, 4% Gelucire 44/14 | 168–182 | 530 | 82 |
| dg-60d | 21% Sorbitan Monopalmitate, 4% Ethocel | 168–180 | 440 | 76 |
| dg-60e | 25% Cetostearyl Alcohol | 183–190 | 390 | 79 |
| dg-60f | 21% Cetostearyl Alcohol, 4% Methocel E4M | 180–188 | 590 | 76 |
| dg-60g | 21% Cetostearyl Alcohol, 4% Gelucire 44/14 | 175–185 | 490 | 76 |
| dg-60h | 21% Cetostearyl Alcohol, 4% Ethocel | 178–190 | 430 | 77 |
| dg-61f | 21% Cetostearyl Alcohol, 4% Methocel E4M | 171–180 | 481 | 80 |

*For each mixed phase co-crystal, only the highest melting point is specified

TABLE 2

Physical Properties of Hydrocortisone Acetate Mixed Phase Co-Crystals

| Lot No. | Assay (% w/w) | Solubility (mcg/mL) | Peak Mp (° C.) | Enthalpy ((−) J/g) | Ingredients | |
|---|---|---|---|---|---|---|
| Control (Intact API) | N/A | 4.5 | 219.92 | 119.05 | Hydrocortisone Acetate | |
| 47A | N/A | 7.0 | 215.84 | 80.51 | Cetostearyl Alcohol, NF | |
| 47D | N/A | 6.9 | 212.14 | 72.59 | Stearic Acid | |
| 57A | N/A | 5.1 | 222.17 | 90.81 | Compritol 888 ATO | |
| 57B | N/A | 2.6 | N/A | N/A | Cetostearyl Alcohol, NF | Emulcire |
| 57C | N/A | 6.1 | 217.31 | 84.84 | Cetostearyl Alcohol, NF | Gelucire 44/14 |
| 57D | N/A | 6.7 | 216.09 | 88.70 | Cetostearyl Alcohol, NF | Povidone |
| 57E | N/A | 6.9 | N/A | N/A | Cetostearyl Alcohol, NF | PVA |
| 57F | N/A | 15.4 | 217.26 | 92.77 | Cetostearyl Alcohol, NF | Methocel E4M |
| 61A | 78.5 | 6.5 | N/A | N/A | Cetostearyl Alcohol, NF | Ethocel |
| 61C | 78.5 | 6.0 | N/A | N/A | Stearic Acid | Ethocel |
| 61D | 76.9 | 6.9 | 212.84 | 89.71 | Stearic Acid | Methocel E4M |
| 63B | 92.1 | 6.9 | 221.82 | 98.36 | Sucrose Ester | |
| 63C | 82.1 | 7.4 | 218.02 | 82.10 | Monosterol | |
| 63H | 91.5 | 6.9 | N/A | N/A | Emulcire | |
| 69B | 86.4 | 24.8 | 217.22 | 90.22 | Cetostearyl Alcohol, NF | Methocel E4M |
| 69C | 89.8 | 13.1 | 216.93 | 88.49 | Cetostearyl Alcohol, NF | Methocel E3 |
| 69D | 89.3 | 12.5 | 218.90 | 87.84 | Monosterol | Methocel E4M |
| 69E | 87.4 | 12.9 | 221.02 | 82.46 | Cetostearyl Alcohol, NF | Methocel E4M |
| 69F | 95.5 | 12.5 | 219.33 | 92.57 | Monosterol | Methocel E3 |
| 69G | 89.8 | 12.7 | 223.88 | 96.32 | Suppercire | Methocel E4M |
| 69H | 91.7 | 11.2 | 222.39 | 92.77 | Suppercire | Methocel E3 |

Tables 3 and 4 demonstrate the physical properties of mixed phase co-crystals of cyclosporin. The materials were prepared by the method described in Example 4. Phospholipon refers to a refined soy derived lecithin.

TABLE 3

The Relative Water Solubility of a Series of Cyclosporin Mixed phase Co-Crystal Powders

| Sample Code No. | Solubility Factor* |
|---|---|
| 93c | 66 |
| 93e | 23 |
| 93i | 15 |
| 94c | 12 |
| 76a | 8 |
| 94e | 5 |
| 93f | 4 |

*Solubility ratio in water at room temperature compared to the amorphous powder solubility.

TABLE 4

Physical Properties of Cyclosporin Mixed Phase Co-Crystals

| Mixed Phase Co-Crystal Lot No. | Description | Melting Point(s) or Glass Transition Point* | Water Solubility (mcg/mL) | Assay (% w/w) |
|---|---|---|---|---|
| 66c | 25% Ethocel | 90–100 | 3.8 | 85.5 |
| 66d | 50% Ethocel | 100–110, 89–104[†] | 4.0 | 61 |
| 66e | 25% Compritol 888 ATO | 80–86 | 4.5 | 69 |
| 66f | 25% Sucrose Ester 1670 | 92–102 | 4.1 | 101 |
| 66g | 25% Stearic Acid | 58–65, 51–61[†] | 3.6 | 85.7 |
| 70b | 25% Sucrose Ester 1670, 25% Methocel E4M | 85–123 | 3.9 | 93.8 |
| 70d | 50% Stearic Acid | 57–59 | 3.2 | 59.5 |
| 70e | 25% Stearic Acid, 25% Ethocel | 55–73 | 3.4 | 57.3 |
| 70f | 25% Cetosterol Alcohol | 46–71 | 3.5 | 81.3 |
| 70g | 25% Phospholipon | 118–139 | 3.7 | 95.4 |
| 70h | 25% Emulcire | 42–80 | 3.5 | 87.3 |
| 71c | 50% Phospholipon | 120–165 | 2.7 | 43.2 |
| 71d | 66% Sucrose Ester 1670 | 90–110 | 3.5 | 36.8 |
| 71e | 25% Phospholipon, 25% Methocel E4M | 104–130 | 3.2 | 54.5 |
| 71f | 33% Povidone | 120–140 | 3.9 | 80.1 |
| 71g | 50% Compritol 888 ATO | 60–65 | 4.1 | 45.8 |

Figure 5:
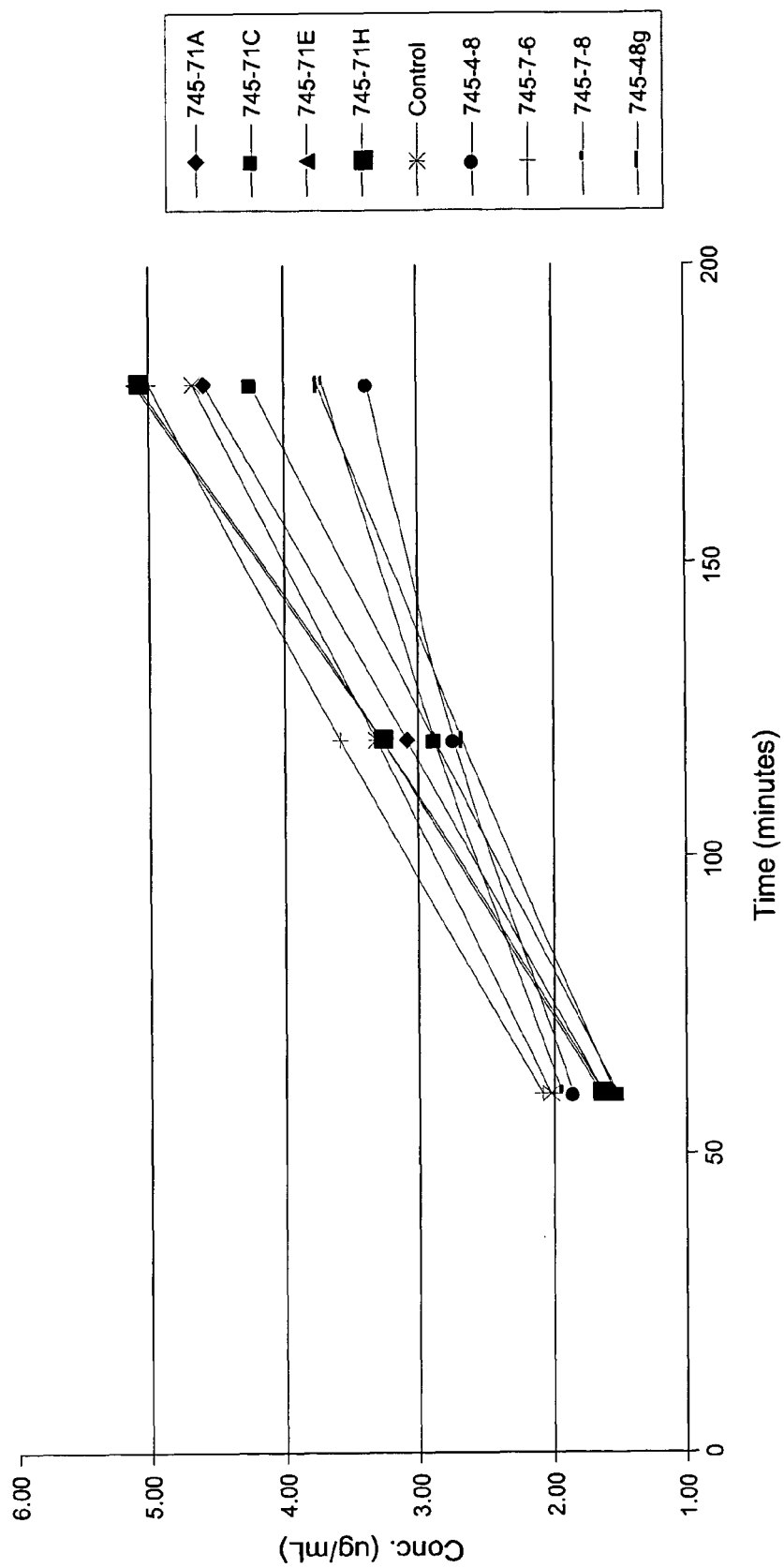
FIG. 5 is a graph showing the intrinsic dissolution rate of itraconazole mixed phase co-crystals in a 3% sodium lauryl sulfate 20% isopropanol:0.1 N HCl (1:1) media.

*For each mixed phase co-crystal, only the highest melting point is specified
[†]Data from duplicate experiments Tables 5 and 6 demonstrate the physical properties of mixed phase co-crystals of itraconazole (see also FIG. 5). To prepare the mixed co-crystals, itraconazole and crystal lattice modifiers were dissolved in DMSO or n-methyl-pyrrolidone or a blend of the two with gentle heating (60° C.) and vortex mixing. The resulting solution was combined with water to intiate the crystallization of the mixed phase co-crystals and vortexed for 18 to 48 hours at room temperature. The mixed phase co-crystals were isolated by filtration, washed with water, and dried.

In the case of 833-2A, -2B, -2C, and -2D, a solution of urea in water (50%) was combined with the solvent phase to initiate crystallization. The resulting suspensions were allowed to mix for 18 to 48 hours at room temperature, collected by filtration, washed with water, and dried.

Capmul MCM C10 refrs to glyceryl monocaprate; SPAN 40 refers to sorbitan palmitate; Pharmalan USP refers to lanolin; Crodesta F10 refers to sucrose distearate; Crodacol C-95 refers to cetyl alcohol; Acylan refrs to Acetylated Lanolin Protalan MOD; SPAN 60 refers to sorbitan monostearate; Crodafos CES refers to dicetyl phosphate, cetearyl alcohol, ceteth-10 phosphate; Polychol 5 refers to laneth-5; Methocel K4M refers to hydoxypropyl methylcellulose; Volpo S-10 refers to steareth-10; and Crodesta F110 refers to sucrose stearate (and) sucrose distearate.

TABLE 5

Intrinsic Dissolution of Itraconazole in 3% Sodium Lauryl Sulfate 20% Isopropanol:0.1 N HCl (1:1)

| Sample Code | Intrinsic Dissolution Rate (mcg/min/cm$^2$) |
|---|---|
| 745-4-8 | 6.4 |
| 745-7-8 | 7.45 |
| 745-48g | 9.15 |
| Control | 11.1 |
| 745-71C | 11.4 |
| 745-71A | 12.4 |
| 745-7-6 | 12.2 |
| 745-71H | 14.4 |
| 833-2A | 55.3 |
| 833-2B | 17.7 |
| 833-2C | 19.3 |
| 833-1A | 19.9 |
| 833-1B | 18.5 |
| 833-1C | 15.4 |
| 833-1D | 8.5 |

TABLE 6

Physical Properties of Itraconazole Mixed Phase Co-Crystals

| Lot No. | Yield (%) | Assay (% w/w) | Solubility (mcg/mL) | Peak Mp (° C.) | Enthalpy ((−) J/g) | Ingredients | | | |
|---|---|---|---|---|---|---|---|---|---|
| Control (Intact API) | N/A | N/A | <.01 | 167.11 | 78.31 | — | — | — | — |
| 745-4-1 | 90.3 | 65.3 | 0.12 | 156.96 | 53.00 | Capmul MCM C10 | SPAN 40 | Stearic Acid | Pharmalan, USP |
| 745-4-2 | 70.5 | 69.8 | 0.02 | 158.21 | 57.87 | Stearic Acid | Crodesta F10 | Pluronic F68 | Crodacol C-95, NF |
| 745-4-3 | 83.0 | N/A | 0.00 | 156.88 | 52.31 | Crodacol C-95, NF | SPAN 40 | Crodacid B | Capmul GMS |
| 745-4-4 | 85.0 | N/A | 0.00 | 156.90 | 56.28 | Acylan | Crodacol C-95, NF | SPAN 60 | Crodacid B |
| 745-4-5 | 78.8 | N/A | 0.02 | 156.82 | 52.10 | Crodafos CES | SPAN 60 | Crodacid B | Stearic Acid |
| 745-4-6 | 77.0 | 74.9 | 0.47 | 161.82 | 65.32 | Crodacid B | Capmul GMS | Crodafos CES | Polychol 5 |
| 745-4-7 | 63.9 | 70.8 | 0.28 | 158.23 | 59.34 | Solutol HS 15 | Stearic Acid | Crodacol C-95, NF | Capmul MCM C10 |
| 745-4-8 | 84.5 | 70.7 | 0.43 | 161.16 | 62.00 | Capmul MCM C10 | SPAN 60 | Crodacid B | Gelucire 44/14 |
| 745-7-1 | 103.0 | N/A | 0.04 | 155.71 | 48.97 | Campul MCM C10 | SPAN 40 | Stearic Acid | Pharmalan, USP | Methocel K4M |
| 745-7-2 | 112.0 | 59.3 | 0.78 | 153.56 | 45.62 | Stearic Acid | Crodesta F10 | Pluronic F68 | Crodacol C-95, NF | Methocel K4M |
| 745-7-3 | N/A | N/A | 0.03 | 152.76 | 46.14 | Crodacol C-95, NF | SPAN 40 | Crodacid B | Capmul GMS | Methocel K4M |
| 745-7-4 | N/A | N/A | 0.27 | 155.67 | 48.28 | Acylan | Crodacol C-95, NF | SPAN 60 | Crodacid B | Methocel K4M |
| 745-7-5 | N/A | 53.7 | 1.00 | 149.88 | 41.93 | Crodafos CES | SPAN 60 | Crodacid B | Stearic Acid | Methocel K4M |
| 745-7-6 | N/A | 49.6 | 0.94 | 153.37 | 43.65 | Crodacid B | Capmul GMS | Cradafos CES | polychol 5 | Methocel K4M |
| 745-7-7 | N/A | 71.7 | 0.90 | 158.69 | 56.56 | Solutol HS 15 | Stearic Acid | Crodacol C-95, NF | Capmul MCM C10 | Methocael K4M |
| 745-7-8 | 90.0 | 73.0 | 0.31 | 161.12 | 58.00 | Capmul MCM C10 | SPAN 60 | Crodacid B | Gelucire 44/14 | Methocel K4M |
| 745-11-1 | 81.3 | N/A | 0.00 | 152.88 | 54.60 | Cholesterol, NF | Dehydrocholic Acid | Crodacid B | SPAN 60 |
| 745-11-2 | 87.8 | N/A | 0.32 | 158.54 | 57.56 | Choles-terol, NF | Capmul MCM C10 | Gelucire 44/14 | Stearic Acid |
| 745-11-3 | 94.3 | N/A | 0.00 | 155.77 | 28.69 | Choles-terol, NF | Dehydrocholic Acid | Compritol 888 ATO | Solutol HS 15 |
| 745-11-4 | 72.0 | 71.3 | 0.93 | 160.06 | 61.21 | Monosteol | Crodacid B | Solutol HS 15 | Capmul MCM C10 |

TABLE 6-continued

Physical Properties of Itraconazole Mixed Phase Co-Crystals

| Lot No. | Yield (%) | Assay (% w/w) | Solubility (mcg/mL) | Peak Mp (° C.) | Enthalpy ((−) J/g) | Ingredients | | | |
|---|---|---|---|---|---|---|---|---|---|
| 745-11-5 | 91.3 | 55.7 | 3.94 | 157.60 | 55.19 | Ceto-stearyl Alcohol, NF | Cholesterol, NF | Monosteol | Solutol HS 15 |
| 745-11-6 | 87.0 | 65.4 | 0.58 | 159.42 | 56.36 | Capmul GMS | Solutol HS 15 | Crodacid B | Monosteol |
| 745-11-7 | 93.3 | N/A | 0.05 | 157.30 | 56.36 | Crodesta F10 | Stearic Acid | Crodacol C-95, NF | Capmul MCM C10 |
| 745-11-8 | 80.5 | N/A | 1.28 | 154.66 | N/A | Solutol HS 15 | Stearic Acid | Crodacol C-95, NF | Dehydrocholic Acid |
| 745-14-1 | 78.1 | N/A | 2.22 | 158.64 | 59.88 | Cetostearyl Alcohol, NF | Cholesterol, NF | Monosteol | Solutol HS 15 |
| 745-14-2 | 87.1 | N/A | 0.00 | 155.06 | 63.46 | Cetostearyl Alcohol, NF | Cholesterol, NF | Monosteol | Dehydrocholic Acid |
| 745-14-3 | 84.2 | N/A | 0.02 | 158.52 | 60.15 | Cetostearyl Alcohol, NF | Cholesterol, NF | Monosteol | Gelucire 44/14 |
| 745-14-4 | 85.3 | N/A | 0.00 | 158.13 | 64.86 | Cetostearyl Alcohol, NF | Cholesterol, NF | Monosteol | Pluronic F68 |
| 745-14-5 | 82.9 | N/A | 0.00 | 160.02 | 64.20 | Cetostearyl Alcohol, NF | Cholesterol, NF | Monosteol | Crodesta F10 |
| 745-14-6 | 79.3 | N/A | 0.78 | 158.87 | 62.33 | Cetostearyl Alcohol, NF | Cholesterol, NF | Monosteol | Volpo S-10 |
| 745-14-7 | 69.8 | N/A | 0.16 | 158.64 | 58.10 | Cetostearyl Alcohol, NF | Cholesterol, NF | Monosteol | Crodesta F10 |
| 745-14-8 | 77.5 | N/A | 0.00 | 159.67 | 69.06 | Cetostearyl Alcohol, NF | Cholesterol, NF | Monosteol | Capmul MCM C10 |
| 745-40-A | 60.8 | N/A | 2.22 | N/A | N/A | Solutol HS 15 | Stearic Acid | Crodacol C-95, NF | Capmul MCM C10 |
| 745-40-B | 86.5 | N/A | 0.00 | N/A | N/A | Cetostearyl Alcohol, NF | Cholesterol, NF | Monosteol | Solutol HS 15 |

Table 7 demonstrates the physical properties of mixed phase co-crystals of intraconazole. To prepare the mixed phase co-crystals, itraconazole and crystal lattice modifiers were dissolved in DMSO or n-methyl-pyrrolidone or a blend of the two with gentle heating (60° C.) and vortex mixing. The resulting solution was combined with water to intiate the crystallization of the mixed phase co-crystals and vortexed for 18 to 48 hours at room temperature. The mixed phase co-crystals were isolated by filtration, washed with water, and dried.

Volpo S-2 refers to steareth-2; Syncrowax AW1-C refers to a hard acid wax; Prolipid 141 refers to a composition of glyceryl stearate, behenyl alcohol, palmitic acid, stearic acid, lecithin, lauryl alcohol, myristyl alcohol, and cetyl alcohol; Liposorb S-4 refers to polysorbate 61; Ganex WP-660 and Ganex V-220 refer to PVP/eicosene copolymers; and Methocel A4K refers to methylcellulose.

TABLE 7

Physical Properties of Itraconazole Mixed Phase Co-Crystals

| Lot No. | Yield (%) | Assay (% w/w) | Solubility (mcg/mL) | Peak Mp (° C.) | Enthalpy ((−) J/g) | Ingredients | | | |
|---|---|---|---|---|---|---|---|---|---|
| Control (Intact API) | N/A | N/A | <.01 | 167.11 | 78.31 | — | — | — | — |
| 745-16-1 | 84.1 | 66.0 | 3.78 | 112.63 | 79.17 | Capmul GMS | Compritol 888 ATO | Crodacid B | Solutol HS 15 |
| 745-16-2 | 94.6 | N/A | 0.20 | 110.87 | 84.38 | Cetostearyl Alcohol, NF | SPAN 60 | Volpo S-2 | Crodacid B |
| 745-16-3 | 98.3 | 76.2 | 1.70 | 120.92 | 75.28 | Cholesterol, NF | Compritol 888 ATO | Dehydrocholic Acid | Volpo S-10 |
| 745-16-4 | 92.1 | N/A | 0.72 | 110.21 | 83.49 | Cholesterol, NF | Dehydrocholic Acid | Monosteol | Volpo S-2 |
| 745-16-5 | N/A | N/A | 0.43 | 104.46 | 72.55 | Volpo S-2 | Volpo S-10 | Cetostearyl Alcohol, NF | Crodacid B |
| 745-16-6 | 92.7 | 86.8 | 3.11 | 113.23 | 92.44 | SPAN 60 | Stearic Acid | Volpo S-2 | Solutol HS 15 |
| 745-16-7 | 99.1 | 88.0 | 1.56 | 112.17 | 91.12 | Cholesterol, NF | Capmul GMS | Cetostearyl Alcohol, NF | Solutol HS 15 |
| 745-16-8 | 94.8 | N/A | 0.78 | 112.49 | 95.38 | Syncrowax AW1-C | Stearic Acid | SPAN 60 | Solutol HS 15 |
| 745-44-A | 58.3 | | 1.74 | 112.95 | 86.48 | Crodacid B | Compritol 888 ATO | Solutol HS 15 | Volpo S-2 |

TABLE 7-continued

Physical Properties of Itraconazole Mixed Phase Co-Crystals

| Lot No. | Yield (%) | Assay (% w/w) | Solubility (mcg/mL) | Peak Mp (° C.) | Enthalpy ((−) J/g) | Ingredients | | | |
|---|---|---|---|---|---|---|---|---|---|
| 745-44-B | 67.7 | | 1.82 | 121.21 | 76.10 | Cholesterol, NF | Compritol 888 ATO | Solutol HS 15 | Dehydrocholic Acid |
| 745-44-C | 62.7 | | 2.54 | 121.52 | 77.63 | Crodesta F160 | Volpo S-2 | Solutol HS 15 | Prolipid 141 |
| 745-44-D | 68.0 | | 1.74 | 122.89 | 78.31 | Capmul GMS | Compritol 888 ATO | Crodacid B | Liposorb S-4 |
| 745-44-E | 53.5 | | 2.33 | 123.66 | 82.42 | Capmul GMS | Compritol 888 ATO | Crodacid B | Solutol HS 15 / Methocel E4M |
| 745-44-F | 72.6 | | 1.15 | 114.27 | 96.29 | Capmul GMS | Compritol 888 ATO | Crodacid B | Solutol HS 15 / Ganex WP-660 |
| 745-44-G | 72.3 | | 1.84 | 123.37 | 81.92 | Capmul GMS | Compritol 888 ATO | Crodacid B | Solutol HS 15 / Methocel A4K |
| 745-44-H | 69.6 | | 1.19 | 114.15 | 87.68 | Capmul GMS | Compritol 888 ATO | Crodacid B | Solutol HS 15 / Ganex V-220F |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of preparing mixed phase co-crystal composition consisting of the steps of:
    (a) forming a first solution of progesterone, hydroxypropyl methylcellulose, and polyoxamer 188 dissolved in ethanol;
    (b) mixing water with the first solution to form a second solution;
    (c) mixing or allowing the second solution to stand for a sufficient period of time to form an initial kinetically favored meta-stable crystalline phase in the second solution,
    (d) forming the thermodynamically favored mixed phase co-crystal composition from the meta-stable crystalline phase by allowing the initial meta-stable crystalline phase to stand or by mixing of the initial meta-stable crystalline phase,
    (e) optionally, isolating the mixed phase co-crystal composition,
    (f) optionally, washing the mixed phase co-crystal composition, and
    (g) optionally, drying the mixed phase co-crystal composition,
    wherein the progesterone, hydroxypropyl methylcellulose, and polyoxamer 188 are contained within the mixed phase co-crystal composition.

* * * * *